(12) United States Patent
Ishii et al.

(10) Patent No.: US 10,856,873 B2
(45) Date of Patent: Dec. 8, 2020

(54) MEDICAL APPARATUS

(71) Applicant: TERUMO KABUSHIKI KAISHA, Tokyo (JP)

(72) Inventors: Naoki Ishii, Isehara (JP); Satoshi Sawada, Hadano (JP); Hideaki Shibata, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 448 days.

(21) Appl. No.: 15/064,240

(22) Filed: Mar. 8, 2016

(65) Prior Publication Data
US 2016/0278780 A1 Sep. 29, 2016

(30) Foreign Application Priority Data

Mar. 27, 2015 (JP) .................. 2015-067178

(51) Int. Cl.
*A61B 17/11* (2006.01)
*A61B 17/00* (2006.01)
*A61B 17/34* (2006.01)

(52) U.S. Cl.
CPC ............ *A61B 17/11* (2013.01); *A61B 17/3468* (2013.01); *A61B 17/3478* (2013.01); *A61B 2017/00566* (2013.01); *A61B 2017/00898* (2013.01); *A61B 2017/1107* (2013.01); *A61B 2017/1132* (2013.01); *A61B 2017/1135* (2013.01); *A61B 2017/1139* (2013.01)

(58) Field of Classification Search
CPC ............... A61B 17/11; A61B 17/3468; A61B 2017/00566; A61B 2017/00898; A61B 2017/1107; A61B 2017/1132; A61B 2017/1135; A61B 2017/1139

USPC .......................................... 606/153
See application file for complete search history.

(56) References Cited

U.S. PATENT DOCUMENTS

| 6,616,675 B1 * | 9/2003 | Evard ................. A61B 1/3137 606/153 |
| 9,023,075 B2 * | 5/2015 | Kassab ............... A61B 17/0057 606/192 |
| 2002/0065524 A1 * | 5/2002 | Miller ................ A61B 17/064 606/139 |

(Continued)

FOREIGN PATENT DOCUMENTS

| JP | 11-501828 A | 2/1999 |
| JP | 2013-234136 A | 11/2013 |
| WO | WO 96/25108 A1 | 8/1996 |

*Primary Examiner* — Kathleen S Holwerda
*Assistant Examiner* — Brooke Labranche
(74) *Attorney, Agent, or Firm* — Buchanan Ingersoll & Rooney PC

(57) ABSTRACT

A medical apparatus for joining body lumens in a living body includes a puncture member having a lumen, a distal opening portion and a needle tip at the distal end of the lumen. The needle tip can puncture a tube wall of the body lumen to form a puncture site. The medical apparatus includes a tubular member in the lumen of the puncture member that expands radially outward and contracts radially inward and a plunger movable relative to the puncture member to release the tubular member from the distal opening portion of the puncture member. The tubular member expands to be fixed to the puncture site when the tubular member is released from the distal opening portion of the puncture member.

18 Claims, 14 Drawing Sheets

(56) References Cited

U.S. PATENT DOCUMENTS

| | | | | |
|---|---|---|---|---|
| 2003/0120292 | A1* | 6/2003 | Park | A61B 17/083 606/153 |
| 2005/0245945 | A1* | 11/2005 | Ewers | A61B 1/00135 606/153 |
| 2005/0251209 | A1* | 11/2005 | Saadat | A61B 17/0401 606/232 |
| 2008/0243151 | A1* | 10/2008 | Binmoeller | A61B 1/00147 606/153 |
| 2010/0121358 | A1* | 5/2010 | Blatter | A61M 39/02 606/155 |
| 2014/0039586 | A1* | 2/2014 | Barker | A61N 1/0551 607/116 |
| 2014/0277050 | A1* | 9/2014 | Andreas | A61B 17/3468 606/185 |

* cited by examiner

[FIG. 1]
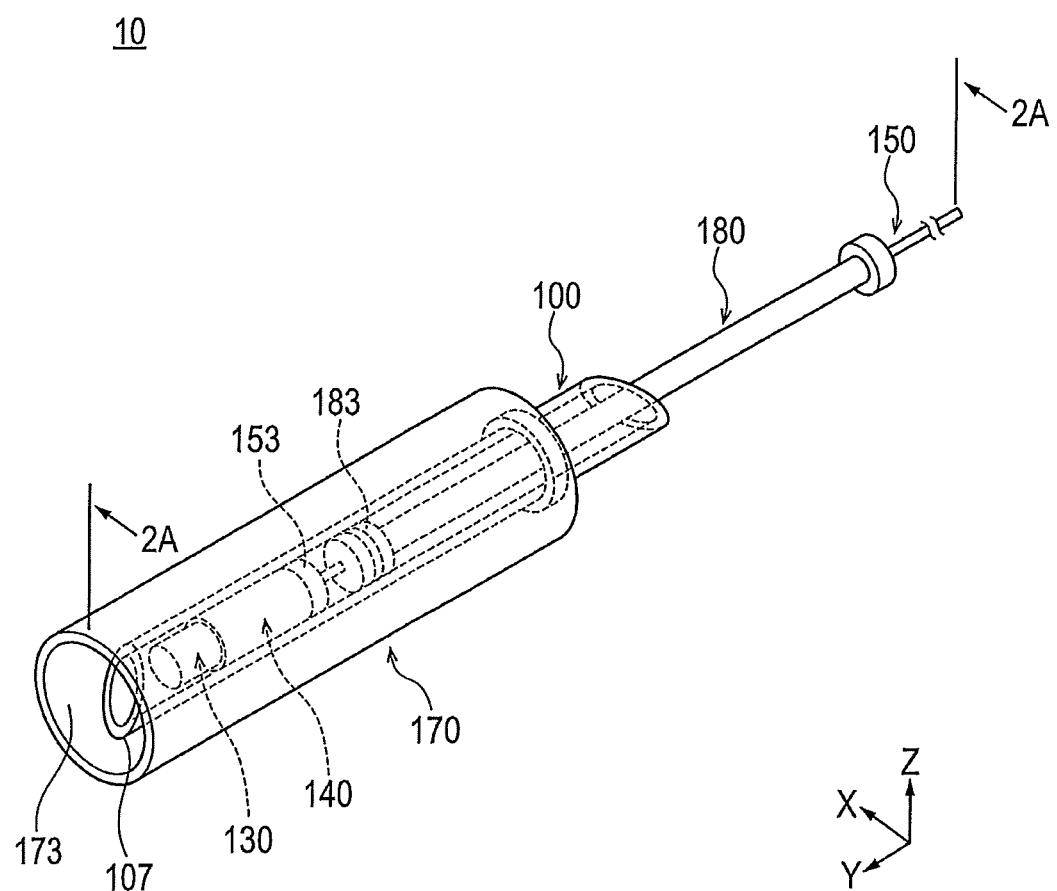

[FIG. 2]
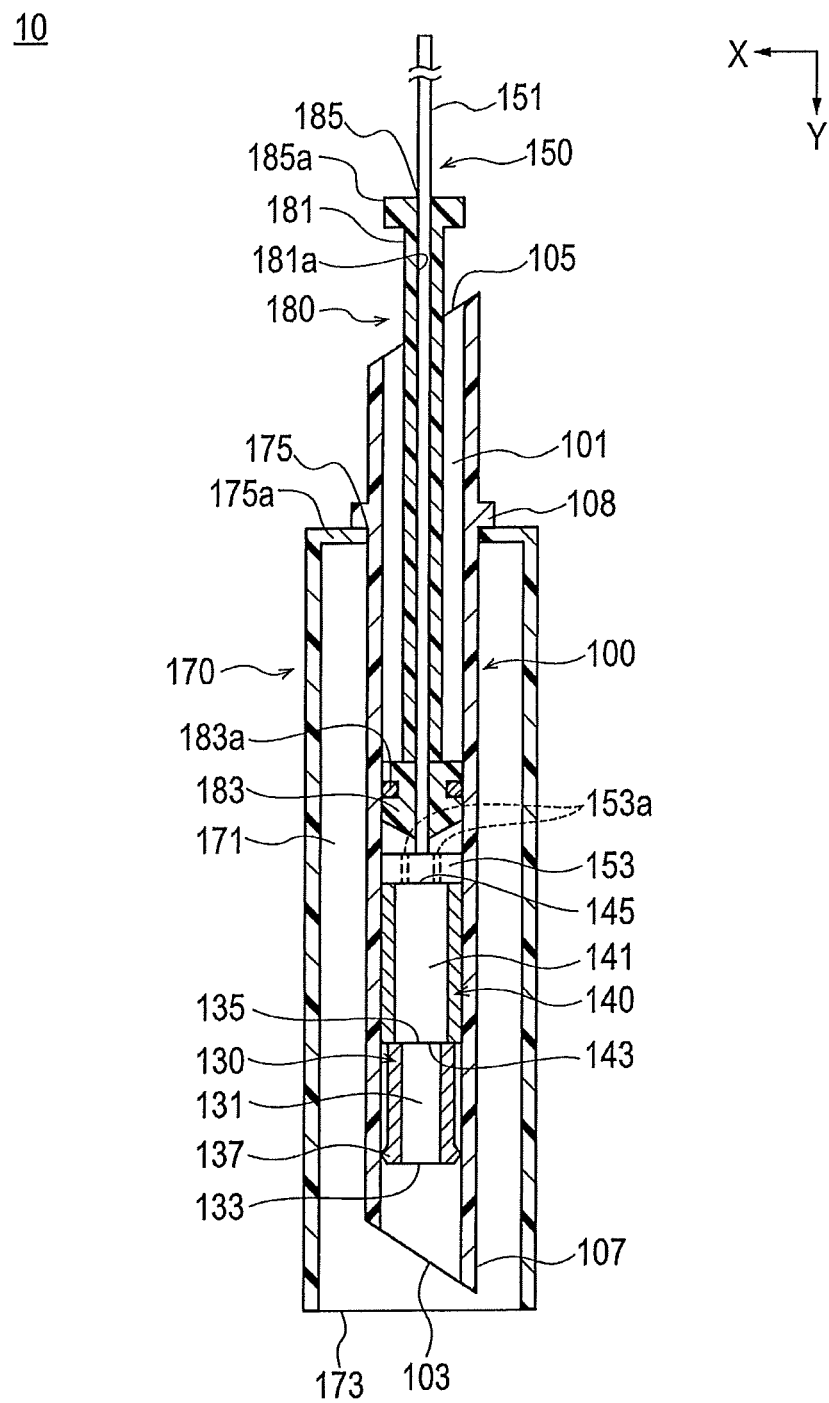

[FIG. 3A]
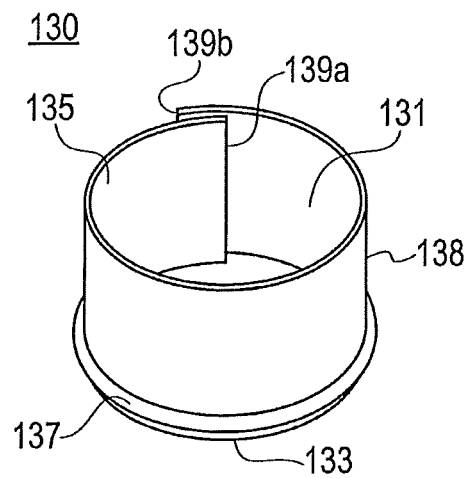
[FIG. 3B]
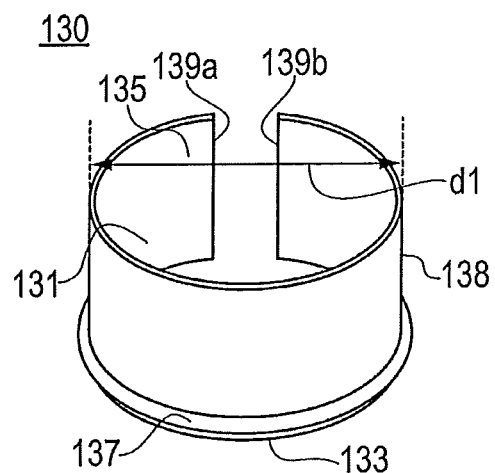
[FIG. 3C]
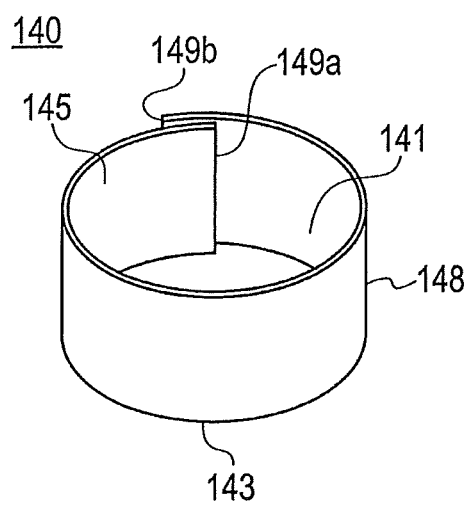
[FIG. 3D]
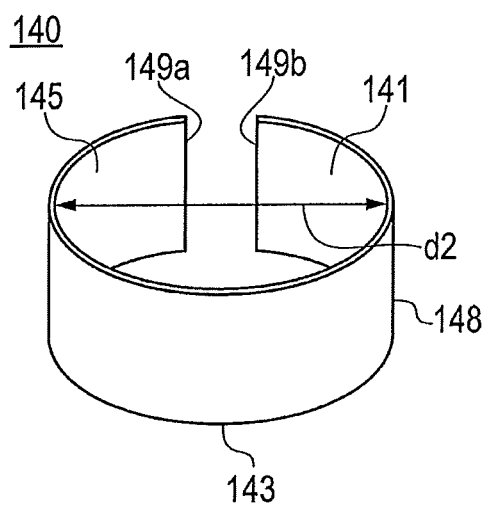

[FIG. 4]
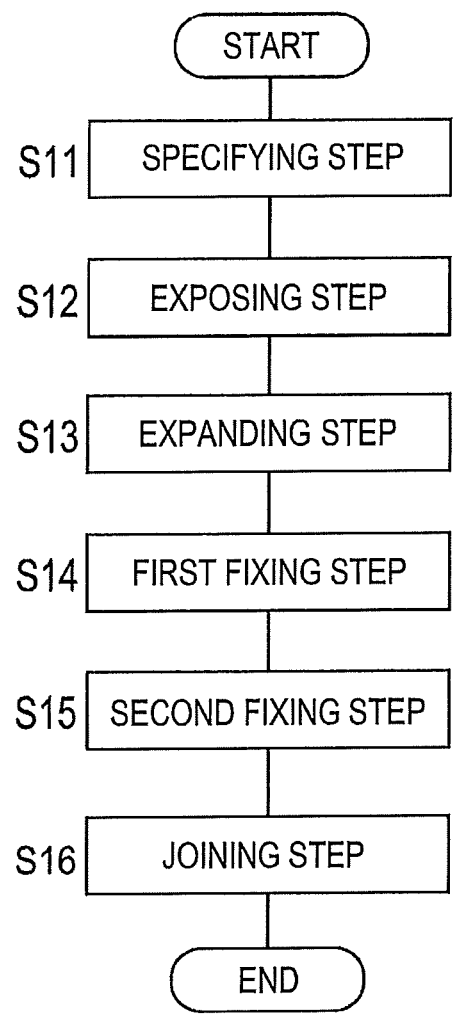

[FIG. 5A]
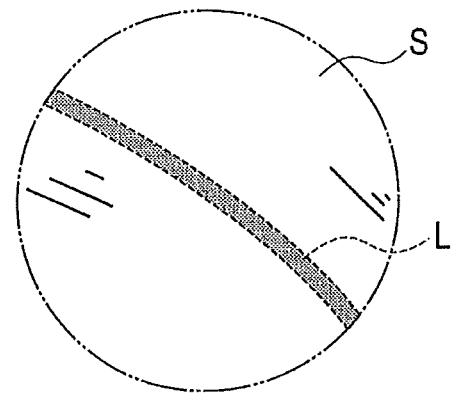
[FIG. 5B]
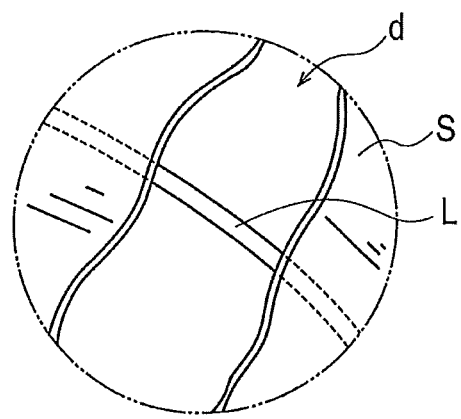
[FIG. 5C]
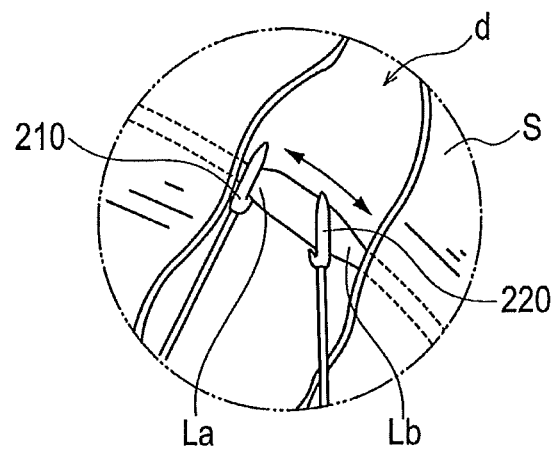

[FIG. 6A]
[FIG. 6B]
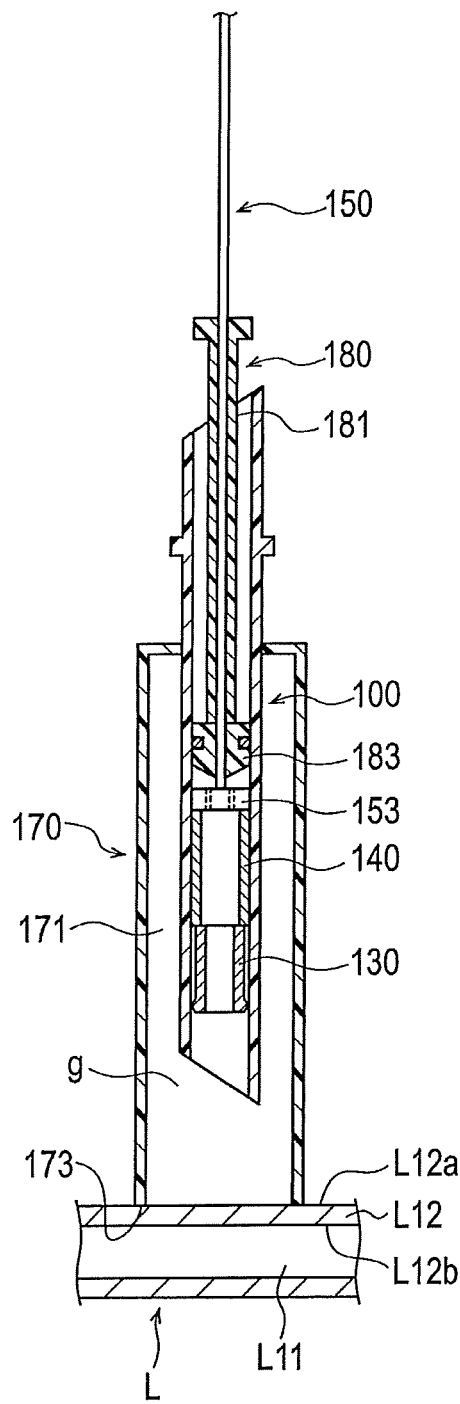
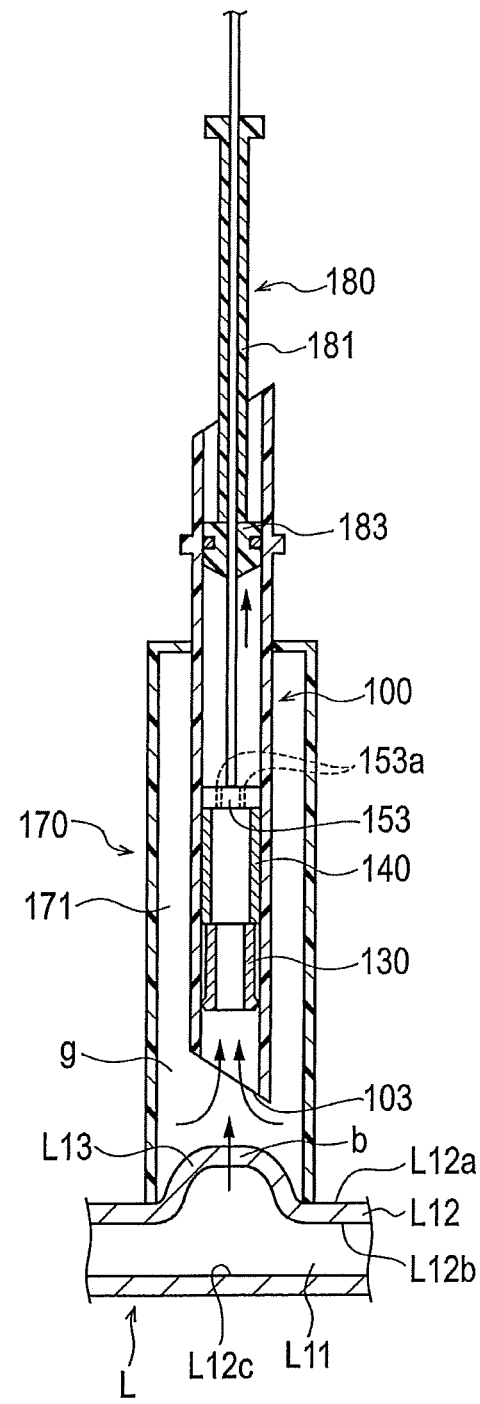

[FIG. 7A]  [FIG. 7B]
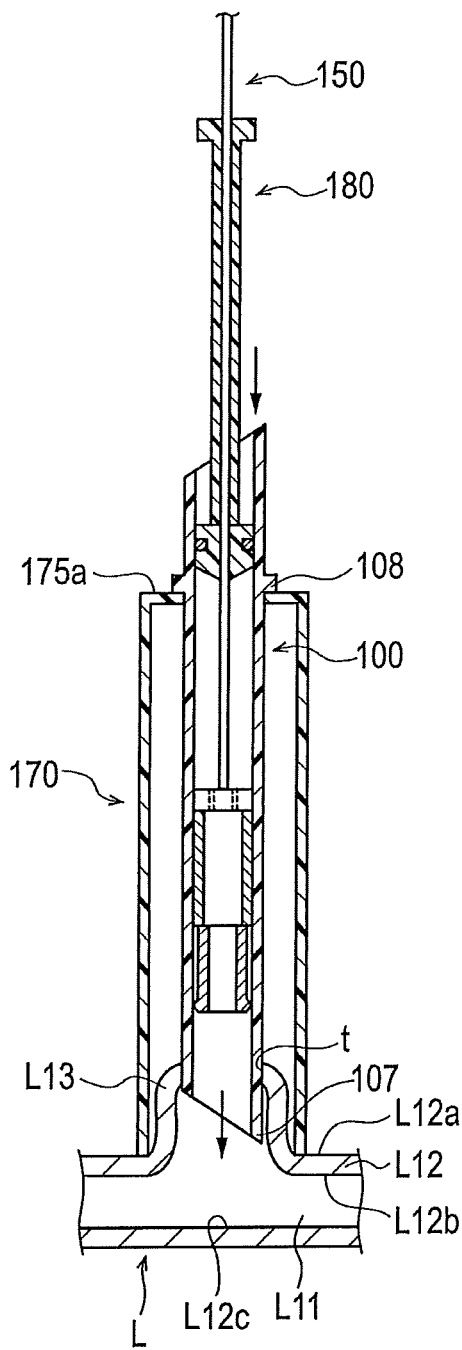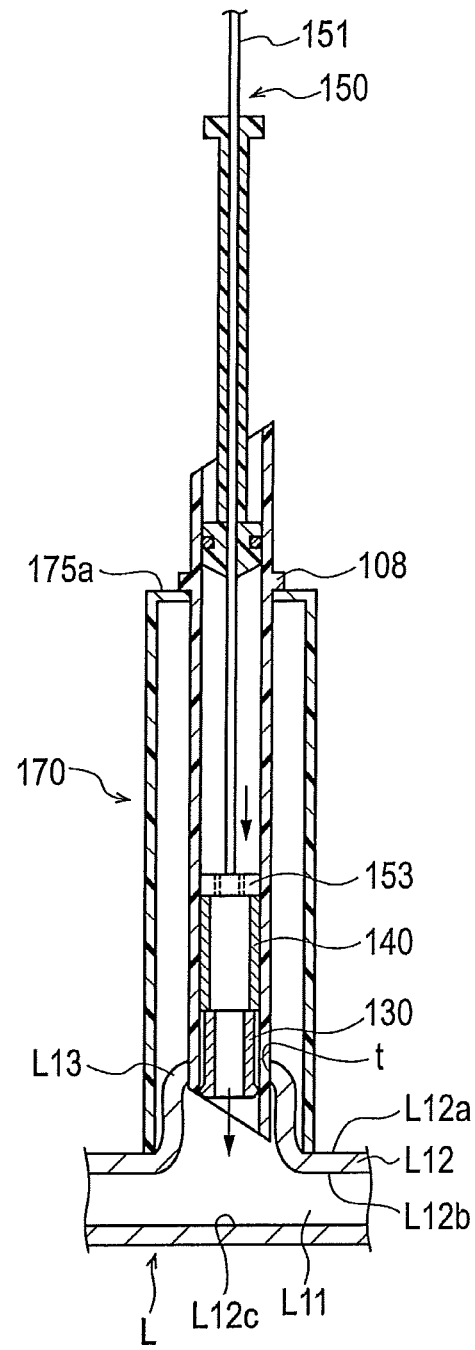

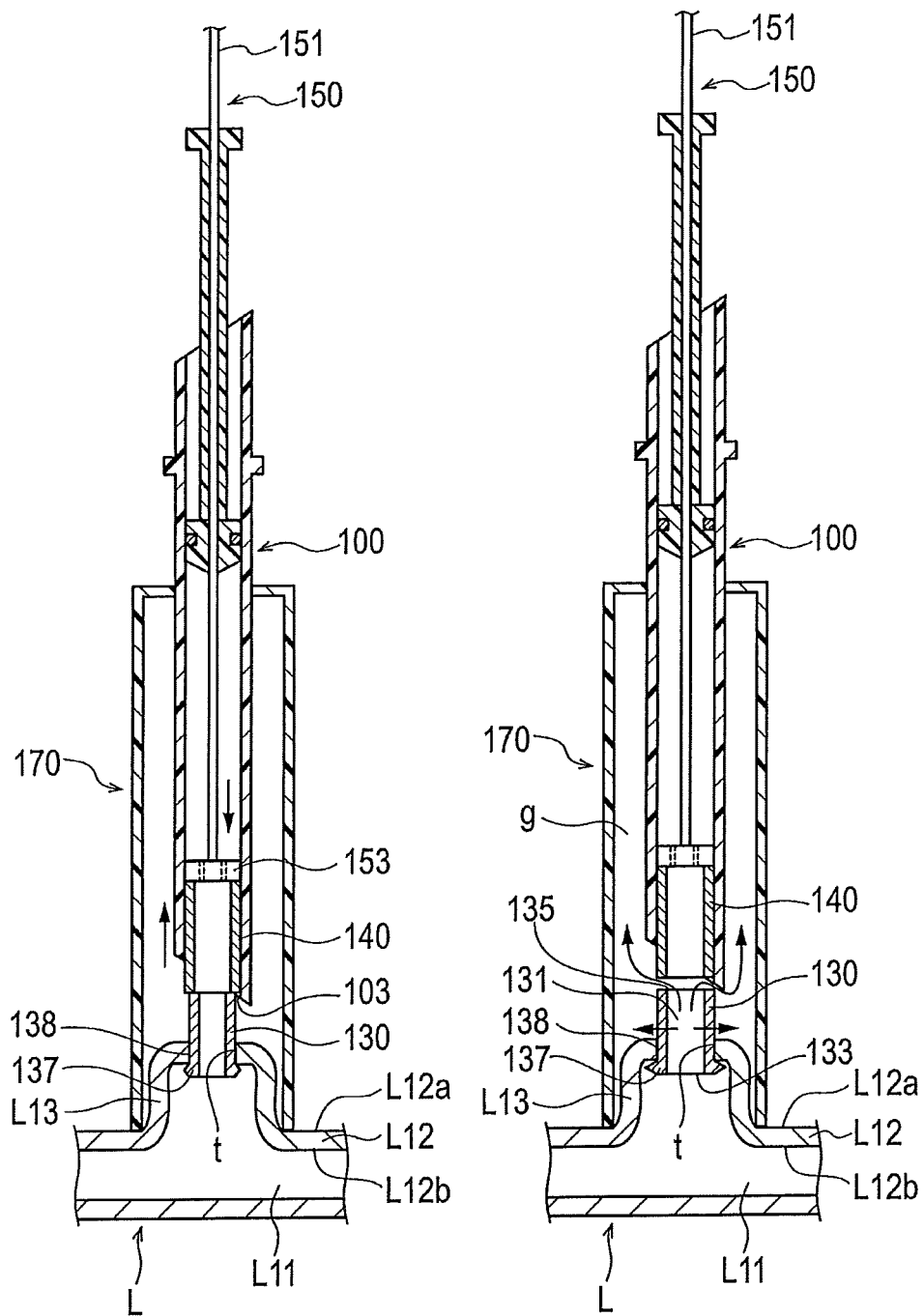

[FIG. 9A]
[FIG. 9B]
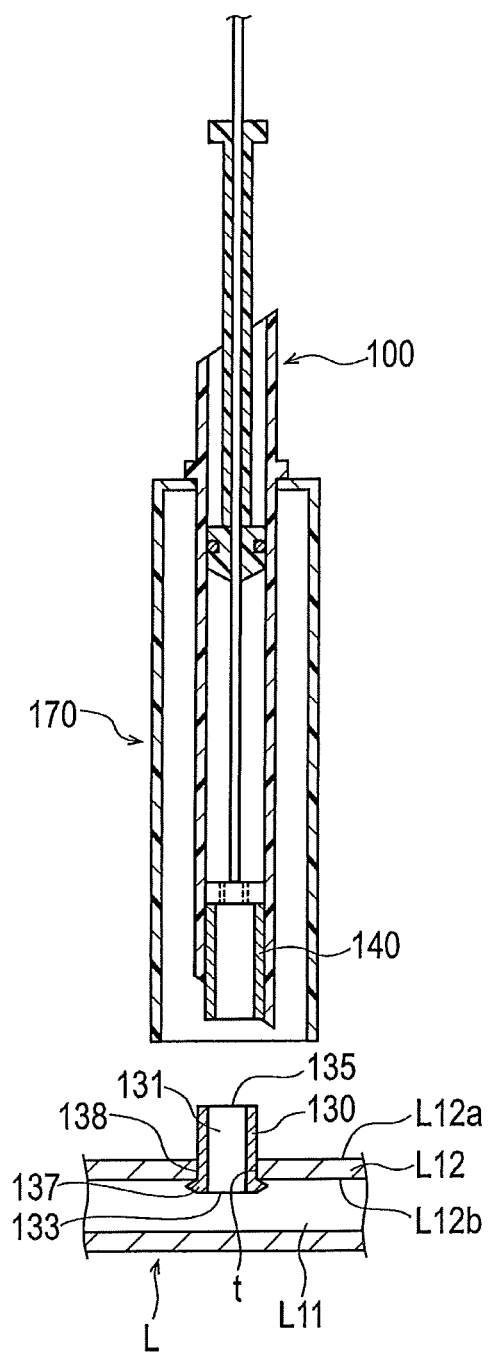
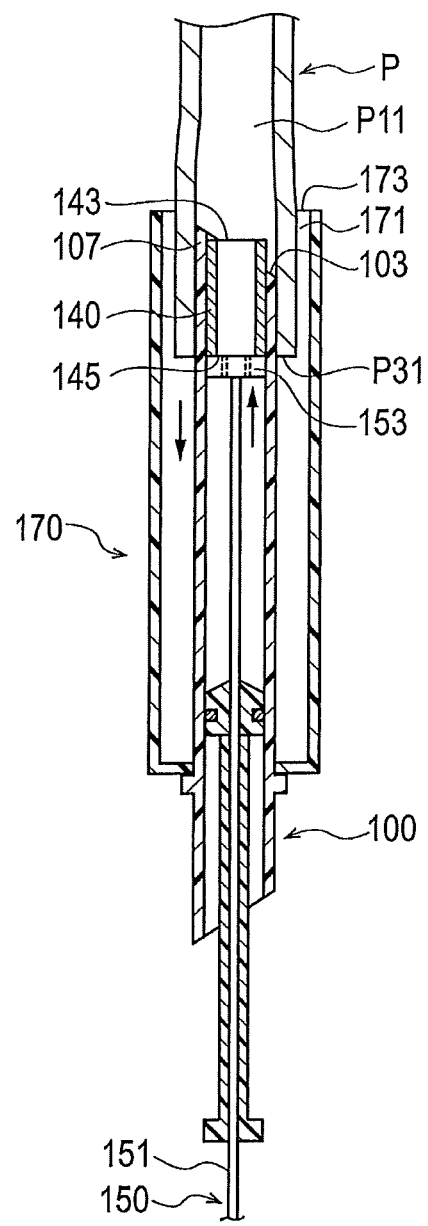

[FIG. 10A]
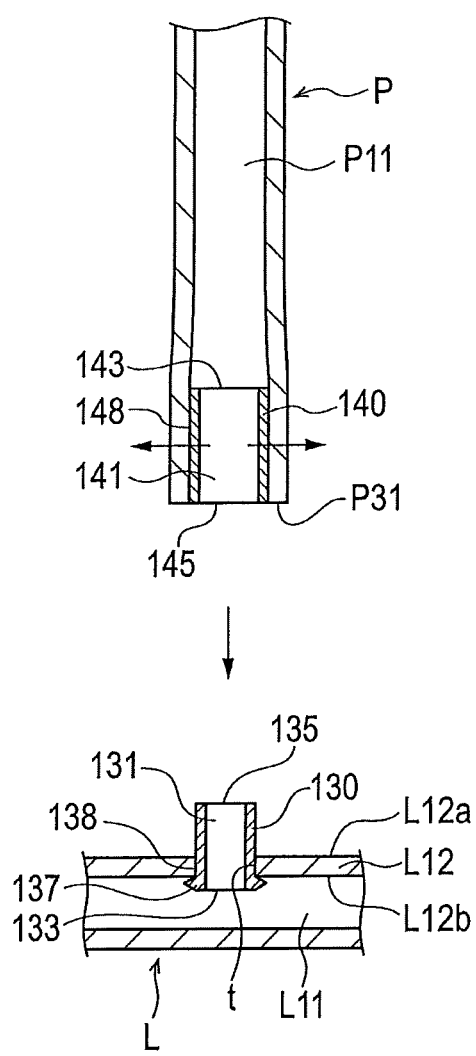
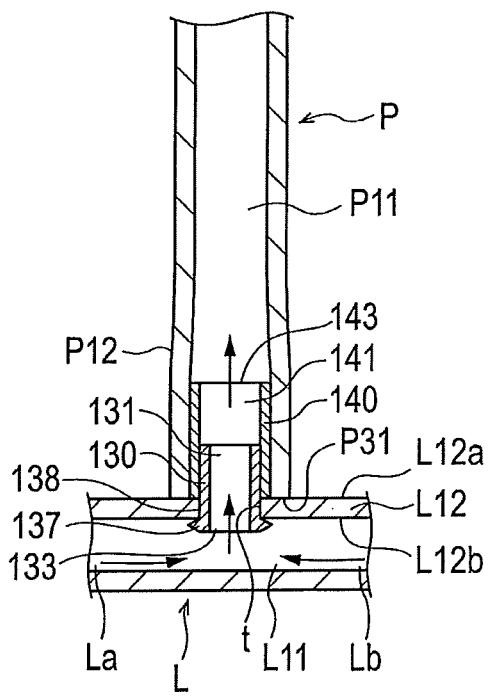
FIG. 10B

[FIG. 11A]
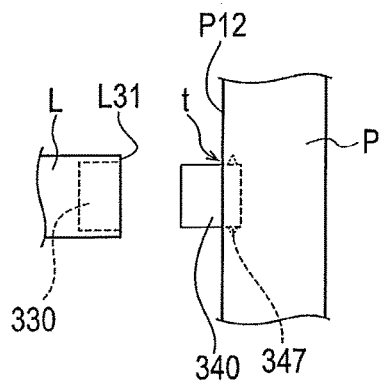
[FIG. 11B]
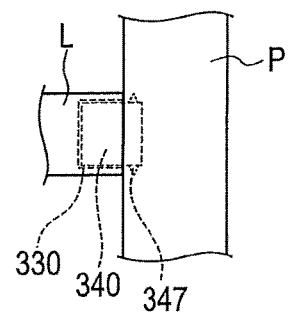
[FIG. 12A]
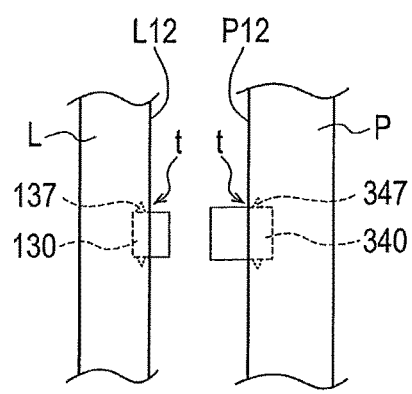
[FIG. 12B]
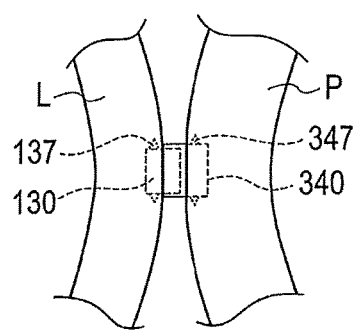
[FIG. 13A]
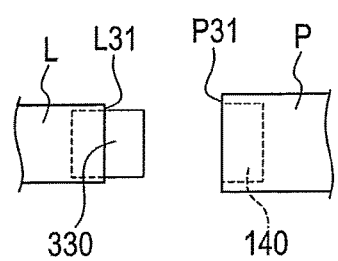
[FIG. 13B]
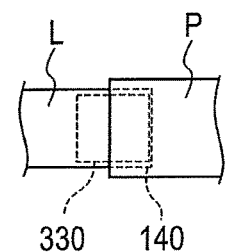

[FIG. 14A]
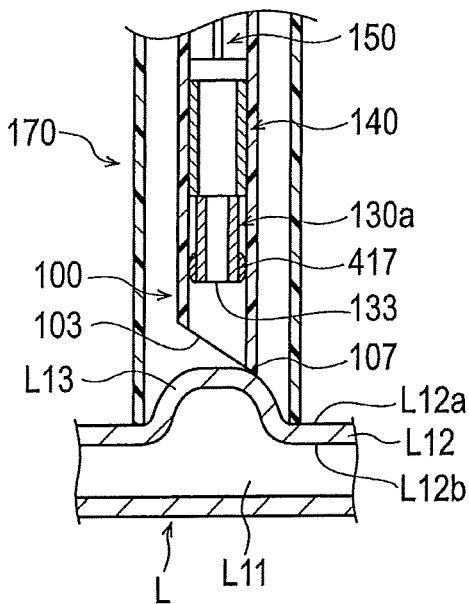
[FIG. 14B]
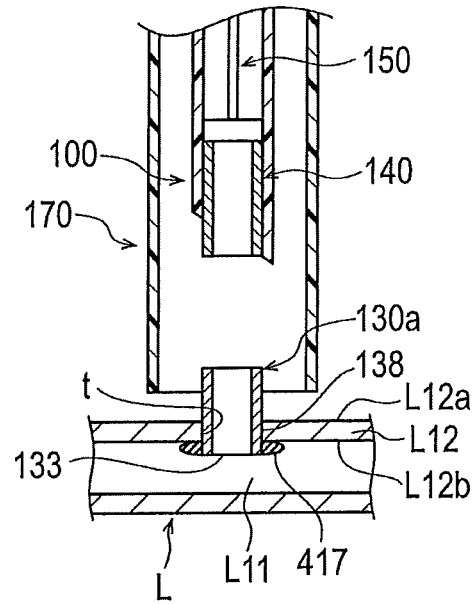
[FIG. 15A]
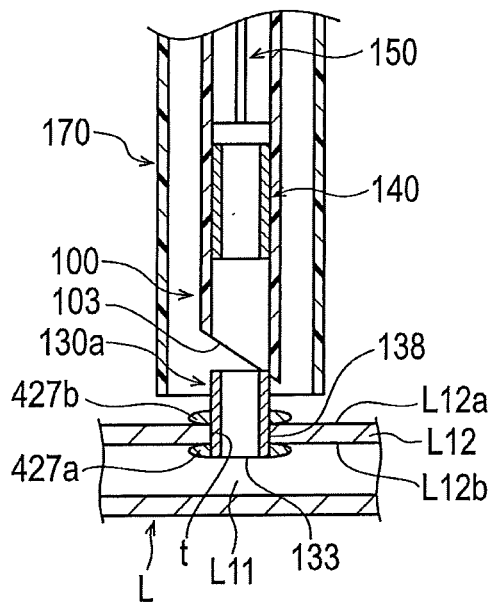
[FIG. 15B]
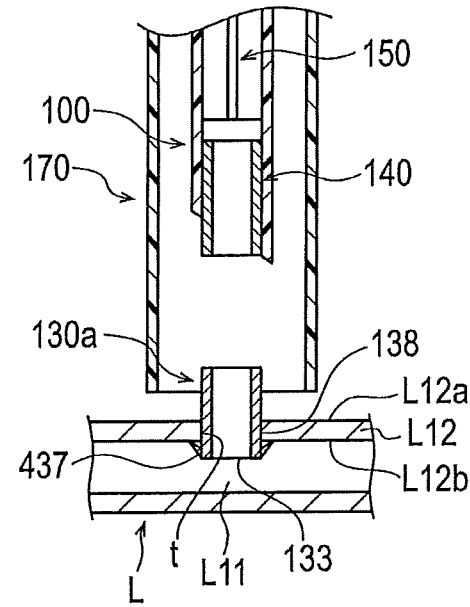

[FIG. 16A]
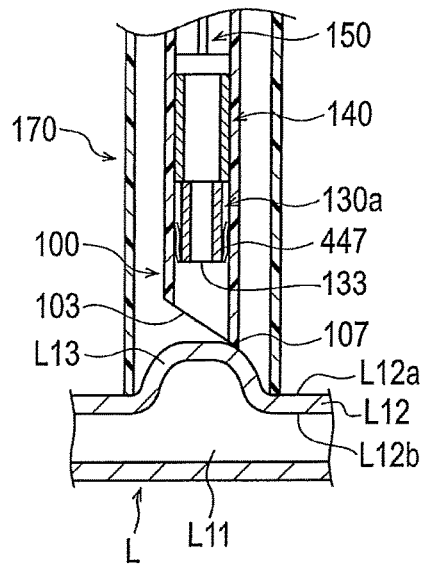
[FIG. 16B]
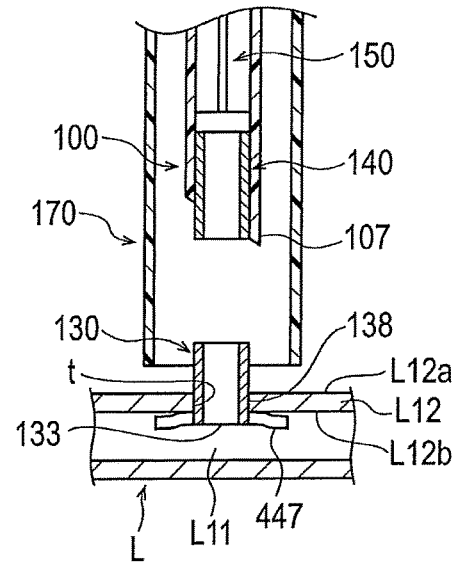
[FIG. 17A]
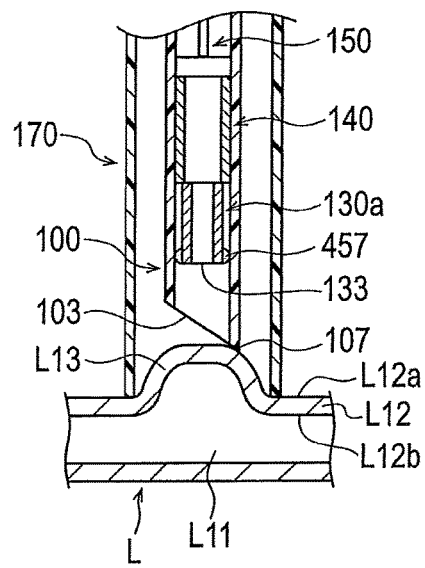
[FIG. 17B]
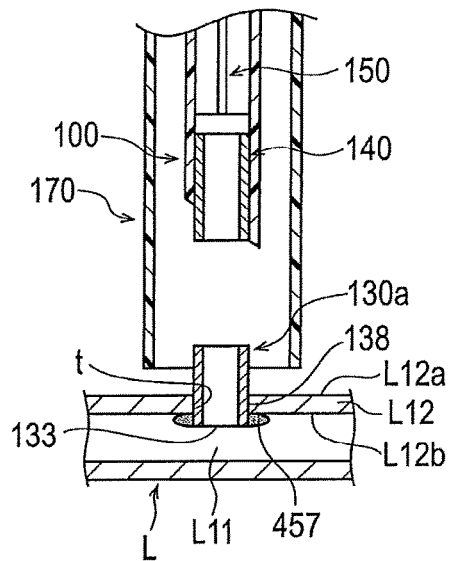

[FIG. 18A]
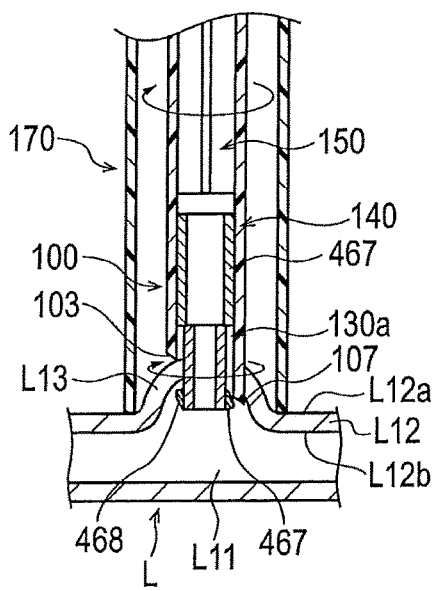
[FIG. 18B]
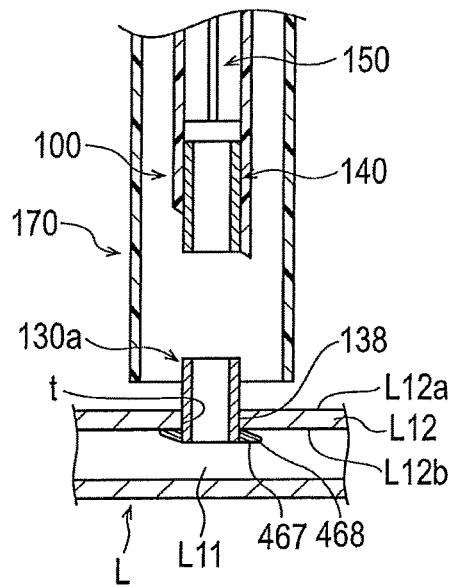
[FIG. 19A]
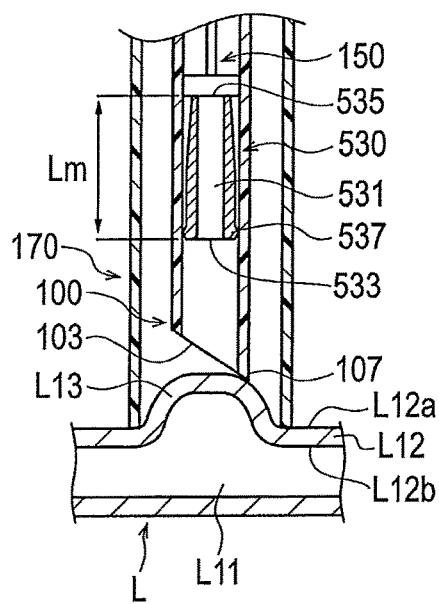
[FIG. 19B]
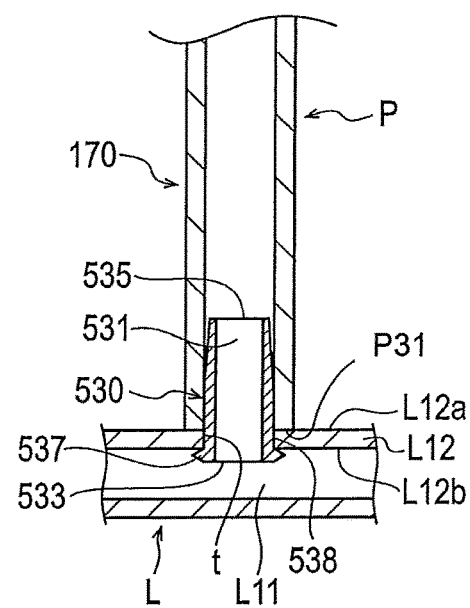

MEDICAL APPARATUS

CROSS-REFERENCES TO RELATED APPLICATIONS

This application is a continuation of Japanese Application No. JP 2015/067178 filed on Mar. 27, 2015, the entire content of which is incorporated herein by reference.

TECHNICAL FIELD

The present invention relates to a medical apparatus which is used for treating lymphedema.

BACKGROUND DISCUSSION

Lymphedema is a disease inside a living body which is developed outside a lymphatic vessel due to local accumulation of lymph (lymphatic fluid). The local accumulation of lymph is caused by congestion of a flow of the lymph flowing inside a lymphatic vessel.

As a method of treating lymphedema, for example, there are known methods such as compression therapy (for example, refer to Japanese Patent Application Publication No. JP-T-11-501828) which alleviates the symptoms by mounting a medical device that applies compression force to each part of a body where edema has occurred due to lymphedema, pharmacotherapy (for example, refer to Japanese Patent Application Publication No. JP-A-2013-234136) which delivers medicine having a therapeutic effect for lymphedema, and lymphaticovenular anastomosis (LVA) in which treatment is realized by performing anastomosis (bypass operation) of a vein and a lymphatic vessel through surgical procedures and causing lymph to flow into the vein. Among the above-referenced treatment methods, the lymphaticovenular anastomosis has recently attracted attention because it exhibits a remarkably high therapeutic effect at the initial stage, that is, the outbreak of lymphedema. The lymphaticovenular anastomosis method also has shown the possibility of achieving complete recovery from lymphedema.

SUMMARY

In lymphaticovenular anastomosis, during anastomosis of a vein and a lymphatic vessel, procedures include cutting a minute window portion (i.e., an aperture) and opening an outer surface of one of the body lumens (for example, the lymphatic vessel), and joining an opening end or a tube wall of the other body lumen (for example, the vein) to the window portion by suturing or the like. However, it is difficult to accurately form the minute window portion without causing unnecessary damage to a lymphatic vessel or a vein with a relatively small diameter. There are thus a limited number of operators who are capable of performing this operation. Even for operators who can perform this operation, the time taken for the procedure is inevitably lengthened.

The medical apparatus disclosed here takes the aforementioned circumstances into consideration. An object of the medical apparatus is to provide a medical apparatus capable of allowing an operator to promptly and easily join a lymphatic vessel and a vein together in a technique of treating lymphedema where the procedure time is shortened.

A medical apparatus according to the invention is used for joining a lymphatic vessel and a vein which are body lumens. The medical apparatus includes a puncture member in which a lumen and a distal opening portion leading to a distal side of the lumen are formed and whose a distal end includes a needle tip for forming a puncture site by puncturing a tube wall of the body lumen, a tubular member that is accommodated in the lumen of the puncture member and is configured to be able to perform expanding deformation radially outward and to perform contracting deformation, and a plunger that is movably inserted into the lumen of the puncture member and releases the tubular member from the distal opening portion of the puncture member in accordance with relative movement with respect to the puncture member. The tubular member is accommodated in the lumen of the puncture member in a contracted state and performs the expanding deformation in accordance with the release from the distal opening portion of the puncture member, to be fixed to the puncture site.

According to the medical apparatus of the invention, a flow of lymph (lymphatic fluid) from the lymphatic vessel to the vein can be formed by fixing the tubular member to the puncture site which is formed by causing the needle tip of the puncture member to puncture the body lumen (lymphatic vessel or vein), and joining the body lumens together via the tubular member. The tubular member which can perform expanding deformation and contracting deformation is used as a member to join the lymphatic vessel and the vein together. Accordingly, it is possible to smoothly perform indwelling in the puncture site which is formed in the body lumen having a relatively small diameter. Moreover, there is no need to form a minute window portion in the body lumen by performing procedures of incision or the like as in lymphaticovenular anastomosis in the related art. Accordingly, it is possible to promptly and easily perform a technique and it is possible to drastically shorten time taken for the technique.

BRIEF DESCRIPTION OF THE DRAWINGS

FIG. 1 is a schematic prospective view illustrating the overall configuration of an embodiment of the medical apparatus.

FIG. 2 is a cross-sectional view of the embodiment of the medical apparatus.

FIGS. 3A to 3D are diagrams illustrating a lymphatic vessel side tubular member (tubular member) and a vein side tubular member (interlocking tubular member) included in the embodiment of the medical apparatus. FIG. 3A is a perspective view illustrating the lymphatic vessel side tubular member in a contracted state, FIG. 3B is a perspective view illustrating the lymphatic vessel side tubular member in an expanded state, FIG. 3C is a perspective view illustrating the vein side tubular member in a contracted state, and FIG. 3D is a perspective view illustrating the vein side tubular member in an expanded state.

FIG. 4 is a diagram illustrating the procedures of a technique for using the first embodiment of the medical apparatus.

FIGS. 5A to 5C are diagrams illustrating examples of procedures in a technique for treating lymphedema.

FIGS. 6A and 6B are cross-sectional views schematically illustrating examples of procedures in the technique using the embodiment of the medical apparatus.

FIGS. 7A and 7B are cross-sectional views schematically illustrating examples of procedures in the technique using the embodiment of the medical apparatus.

FIGS. 8A and 8B are cross-sectional views schematically illustrating examples of procedures in the technique using the embodiment of the medical apparatus.

FIGS. 9A and 9B are cross-sectional views schematically illustrating examples of procedures in the technique using the embodiment of the medical apparatus.

FIGS. 10A and 10B are cross-sectional views schematically illustrating examples of procedures in the technique using the embodiment of the medical apparatus.

FIGS. 11A and 11B are diagrams schematically illustrating a procedure of end-to-side anastomosis using the lymphatic vessel side tubular member and the vein side tubular member.

FIGS. 12A and 12B are diagrams schematically illustrating a procedure of side-to-side anastomosis using the lymphatic vessel side tubular member and the vein side tubular member.

FIGS. 13A and 13B are diagrams schematically illustrating a procedure of end-to-end anastomosis using the lymphatic vessel side tubular member and the vein side tubular member.

FIGS. 14A and 14B are cross-sectional views schematically illustrating a usage example of the lymphatic vessel side tubular member of Modification Example 1.

FIG. 15A is a cross-sectional view schematically illustrating a usage example of the lymphatic vessel side tubular member of Modification Example 2, and FIG. 15B is a cross-sectional view schematically illustrating a usage example of the lymphatic vessel side tubular member of Modification Example 3.

FIGS. 16A and 16B are cross-sectional views schematically illustrating usage examples of the lymphatic vessel side tubular member of Modification Example 4.

FIGS. 17A and 17B are cross-sectional views schematically illustrating usage examples of the lymphatic vessel side tubular member of Modification Example 5.

FIGS. 18A and 18B are cross-sectional views schematically illustrating usage examples of the lymphatic vessel side tubular member of Modification Example 6.

FIGS. 19A and 19B are cross-sectional views schematically illustrating usage examples of the tubular member of an alternative embodiment.

DETAILED DESCRIPTION

Set forth below is a detailed description of an embodiment of a medical apparatus and method representing an example of the inventive medical apparatus and method disclosed here. The dimension ratios in the drawings are exaggerated for convenience of description/illustration, and thus, the dimension ratios may be different from the actual ratios.

FIG. 1 is a schematic perspective view illustrating a medical apparatus of an embodiment. FIG. 2 is a cross-sectional view of the medical apparatus taken along line 2A-2A indicated in FIG. 1. FIGS. 3A to 3D are perspective views illustrating lymphatic vessel side tubular members and vein side tubular members included in the medical apparatus. FIG. 4 is a diagram illustrating the procedures of a technique for using the medical apparatus. FIGS. 5A to 5C are diagrams schematically illustrating a procedure of the technique when performing incision of a target lesion. FIGS. 6A to 10B are diagrams that illustrate examples of procedures in the technique using the medical apparatus.

A medical apparatus 10 according to the present embodiment is configured to treat lymphedema. The medical apparatus 10 is capable of treating and alleviating symptoms of lymphedema by joining a lymphatic vessel L and a vein P (i.e., a bypass operation, e.g., see FIGS. 10A and 10B) of a patient who is affected by lymphedema.

As illustrated in FIGS. 1 and 2, the medical apparatus 10 generally includes a puncture member 100 which has a needle tip 107 capable of puncturing a tube wall of a body lumen, a lymphatic vessel side tubular member (i.e., a tubular member) 130 and a vein side tubular member (i.e., an interlocking tubular member) 140, and a plunger 150 for operating/moving each of the tubular members 130, 140 accommodated inside the puncture member 100. The lymphatic vessel side tubular member 130 and the vein side tubular member 140 are joining members to join the lymphatic vessel L and the vein P.

As described below, the lymphatic vessel side tubular member 130 indwells in the lymphatic vessel L in a fixed state by operating the puncture member 100 and the plunger 150 in the technique for using the medical apparatus 10 (e.g., as illustrated in FIG. 8A). After fixing the vein side tubular member 140 to the vein P, the tubular members 130, 140 are interlocked with one another, thereby joining the lymphatic vessel L and the vein P together (e.g., as illustrated in FIG. 10B). When the lymphatic vessel L and the vein P are joined together, it is possible to induce lymph flowing from the lymphatic vessel L toward the vein P. This technique with the medical apparatus 10 can treat and alleviate the symptoms of lymphedema. In the description of this specification, the lymphatic vessel L and the vein P which are joining targets may be referred to using the generic term "body lumen."

First, the configurations of portions of the medical apparatus 10 will be individually described in detail.

In the description of the medical apparatus 10, a side where the needle tip 107 of the puncture member 100 is formed (lower side in FIG. 2) is considered to be a distal side, a side opposite to the side where the needle tip 107 of the puncture member 100 is formed (upper side in FIG. 2) is considered to be a proximal side, and an extending direction of the puncture member 100 (i.e., the vertical direction in FIG. 2) is considered to be an axial direction. The X-axis labeled on FIGS. 1 and 2 indicates a width direction of the medical apparatus 10, and the Y-axis labeled on FIGS. 1 and 2 indicates the axial direction of the medical apparatus 10. The Z-axis labeled on FIG. 1 indicates a direction orthogonal to a plane formed by the X-axis and the Y-axis.

As illustrated in FIGS. 1 and 2, the puncture member 100 is configured to be a hollow member. The puncture member 100 includes a lumen 101 extending in the axial direction of the puncture member 100, a distal opening portion 103 opening at the distal side of the lumen 101, and a proximal opening portion 105 opening at the proximal side of the lumen 101. The distal end of the distal opening portion 103 positioned is shaped or formed as the needle tip 107. The needle tip 107 is capable of puncturing the tube wall of a body lumen.

The needle tip 107 of the puncture member 100 is circularly formed in a front view when viewed from the distal side (i.e., the needle tip 107 is circularly shaped when viewed from the distal side). Therefore, a puncture site (i.e., a puncture hole) t, which is formed when the needle tip 107 punctures a lymphatic vessel L, is circularly formed in a front view (i.e., the puncture site is circularly shaped). The lymphatic vessel side tubular member 130 has a substantially cylindrical outer shape (i.e., the shape of an axially orthogonal cross section of the lymphatic vessel side tubular member 130 is circular), so as to be insertable into the puncture site t (e.g., refer to FIGS. 3A and 3B). The cross-sectional shape, the sharpness (puncturing characteristics), the outer diameter, and the like of the needle tip 107 are not particularly limited as long as it is possible to form the puncture site t in which the lymphatic vessel side tubular member 130 can be fixed.

For example, the puncture member 100 can be made from a known resin material or a known metal material having biocompatibility. It is preferable that the puncture member 100 has predetermined hardness to ensure the needle tip 107 possesses sufficient puncturing characteristics. Examples of the material of the puncture member 100 include a resin material such as polypropylene, polyethylene, polyethylene terephthalate, polymethyl methacrylate, polycarbonate, polyether ether ketone, polyether ketone ketone, polytetrafluoroethylene, a tetrafluoroethylene-perfluoroalkyl vinyl ether copolymer, a tetrafluoroethylene-hexafluoropropylene copolymer, a tetrafluoroethylene-ethylene copolymer, PVDF (polyvinylidene fluoride), polychlorotrifluoroethylene, a chlorotrifluoroethylene-ethylene copolymer, and an ultraviolet curing resin; and a metal material such as SUS, NiTi, and CoCr; glass; or ceramics. When the puncture member 100 is made from a resin material, it is preferable to form a transparent or translucent puncture member 100 to improve the technique efficiency by allowing the inside of the puncture member 100 to be visually recognized (i.e., visible) from the outside.

As illustrated in FIG. 2, when the medical apparatus 10 is used, the lymphatic vessel side tubular member 130 and the vein side tubular member 140 are disposed in the lumen 101 of the puncture member 100 in order from the distal side (i.e., the lymphatic vessel side tubular member 130 is located distally of the vein side tubular member 140). The plunger 150 and a negative pressure generation member 180 (described below) are inserted through the lumen 101 of the puncture member 100. A predetermined outer tube 170 is disposed on and around the outer circumference of the puncture member 100 so as to cover the puncture member 100.

The plunger 150 includes a rod-like main body portion 151 and a push-in portion 153 at the distal end of the main body portion 151. The plunger 150 applies pressing force for moving each of the tubular members 130, 140 toward the distal side. A user (i.e., an operator or the like) who uses the medical apparatus 10 can move each of the tubular members 130 and 140 forward to the distal side of the puncture member 100 (i.e., the user can distally move the tubular members 130, 140 within the puncture member 100) by grasping the main body portion 151 with fingers and the like and moving the plunger 150 forward (i.e., towards the distal end). Thus, the user can perform an operation of pushing out (i.e., a discharging operation) each of the tubular members 130, 140 from the lumen 101.

As illustrated in FIG. 2, before being fixed to the lymphatic vessel L, the lymphatic vessel side tubular member 130 is accommodated in the lumen 101 of the puncture member 100 in a contracted state. Similarly, before being fixed to the vein P, the vein side tubular member 140 is accommodated in the lumen 101 of the puncture member 100 in a contracted state.

FIG. 3A illustrates the lymphatic vessel side tubular member 130 in the contracted state and FIG. 3B illustrates the lymphatic vessel side tubular member 130 in the expanded state.

The lymphatic vessel side tubular member 130 is a hollow member including a lumen 131, a side wall 138 which surrounds the lumen 131, a distal opening portion 133 at the distal end of the lumen 131, a proximal opening portion 135 at the proximal end of the lumen 131, and a pair of separated ends 139a, 139b. The separated ends 139a, 139b are formed by cutting and opening the side wall 138 (i.e., there is a slit from the top edge through the bottom edge of the side wall 138).

When being accommodated inside the lumen 101 of the puncture member 100, the lymphatic vessel side tubular member 130 is deformed (i.e., contracted) such that the separated ends 139a and 139b overlap one another in response to being pushed into the lumen 101. Deforming the lymphatic vessel side tubular member 130 causes the overall shape to contract (i.e., the lymphatic vessel side tubular member 130 decreases in outer diameter/contracts radially inwards when deformed/contracted). When being released from the lumen 101 of the puncture member 100, the lymphatic vessel side tubular member 130 deforms (i.e., expands radially outward) to cause the separated ends 139a, 139b to separate from each other and not overlap in response to the removal of the binding/contracting force applied by an inner surface of the puncture member 100. The removal of the binding force on the vessel side tubular member 130 applied by the inner surface of the puncture member 100 thus causes the overall shape of the vessel side tubular member 130 to expand (i.e., the outer diameter of the vessel side tubular member 130 increases).

As described above, since the separated ends 139a and 139b are formed by cutting and opening the side wall 138 of the lymphatic vessel side tubular member 130, expanding deformation (i.e., radially outward expansion) and contracting deformation (i.e., radially inward contraction) of the lymphatic vessel side tubular member 130 can be smoothly performed when the lymphatic vessel side tubular member 130 is inserted into the lumen 101 of the puncture member 100 and when the lymphatic vessel side tubular member 130 is released from the lumen 101 of the puncture member 100.

FIG. 3C illustrates the vein side tubular member 140 in a contracted state and FIG. 3D illustrates the vein side tubular member 140 in an expanded state.

The vein side tubular member 140 is a hollow member including a lumen 141, a side wall 148 which surrounds the lumen 141, a distal opening portion 143 at the distal end of the lumen 141, a proximal opening portion 145 at the proximal end of the lumen 141, and a pair of separated ends 149a, 149b. The separated ends 149a, 149b are formed by cutting and opening the side wall 148.

Similar to the lymphatic vessel side tubular member 130, when being accommodated inside the lumen 101 of the puncture member 100, the vein side tubular member 140 is deformed (i.e., contracted) such that the separated ends 149a, 149b overlap one another, thereby causing the overall shape to contract (i.e., the vein side tubular member 140 decreases in outward diameter/contracts radially inward). When being released from the lumen 101 of the puncture member 100, the vein side tubular member 140 deforms (i.e., expands radially outward) to cause the separated ends 149a, 149b to separate from one another in response to removal of the binding/contracting force applied by the inner surface of the puncture member 100. The removal of the binding force on the vein side tubular member 140 applied by the inner surface of the puncture member 100 thus causes the overall shape of the vein side tubular member 140 to expand (i.e., the outer diameter of the vein side tubular member 140 increases). Accordingly, expanding deformation (i.e., radially outward expansion) and contracting deformation (i.e., radially inward contraction) of the vein side tubular member 140 can be smoothly performed when the vein side tubular member 140 is inserted into the lumen 101 of the puncture member 100 and when the vein side tubular member 140 is released from the lumen 101 of the puncture member 100.

As illustrated in FIG. 10A, when indwelling in the lymphatic vessel L, the lymphatic vessel side tubular member 130 is inserted into the puncture site t in the lymphatic vessel L. The lymphatic vessel side tubular member 130 causes expanding deformation force to act in a state of being inserted into the puncture site t so that the lymphatic vessel side tubular member 130 is tightly fixed to the inner surface of the puncture site t (i.e., the lymphatic vessel side tubular member 130 expands radially outwardly when inserted into the puncture site t). Meanwhile, the vein side tubular member 140 is inserted into a lumen P11 of the vein P. The vein side tubular member 140 causes expanding deformation force to act when being inserted into the lumen P11 of the vein P so that the vein side tubular member 140 is tightly fixed to the inner surface of the vein P (i.e., the vein side tubular member 140 expands radially outwardly when inserted into the lumen P11 of the vein).

As illustrated in FIG. 10B, when joining the lymphatic vessel L and the vein P together, a proximal portion of the lymphatic vessel side tubular member 130 which is exposed from the puncture site t formed in the lymphatic vessel L is inserted into the lumen 141 of the vein side tubular member 140 that is in the lumen P11 of the vein P. The lymphatic vessel side tubular member 130 and the vein side tubular member 140 are mechanically interlocked with each other through this technique. It is thus possible to join the lymphatic vessel L and the vein P together by performing the simple operation or technique of interlocking the lymphatic vessel side tubular member 130 and the vein side tubular member 140 with each other.

It is preferable that a diameter (inner diameter) d2 of the lumen of the vein side tubular member 140 after expanding deformation illustrated in FIG. 3D is formed to be greater than an outer diameter d1 of the lymphatic vessel side tubular member 130 after expanding deformation illustrated in FIG. 3B.

Forming the inner diameter d2 of the vein side tubular member 140 and the outer diameter d1 of the lymphatic vessel side tubular member 130 to have the above-described dimensional relationship, can prevent the tube wall P12 of the vein P from being pinched between the lymphatic vessel side tubular member 130 and the vein side tubular member 140 (refer to FIG. 10B) when the lymphatic vessel side tubular member 130 has been inserted into the lumen 141 of the vein side tubular member 140 and the lymphatic vessel L and the vein P are joined together. Accordingly, the lymphatic vessel side tubular member 130 and the vein side tubular member 140 can be smoothly interlocked with each other. However, since the interlocking force between the lymphatic vessel side tubular member 130 and the vein side tubular member 140 basically depends on the friction force acting between the outer surface of the lymphatic vessel side tubular member 130 and the inner surface of the vein side tubular member 140, it is not preferable to cause the outer diameter d1 of the lymphatic vessel side tubular member 130 to be significantly smaller than the inner diameter d2 of the vein side tubular member 140. In consideration of the above-described points, the outer diameter d1 of the lymphatic vessel side tubular member 130 after expanding deformation (i.e., radially outward expansion) can be preferably formed within a range from 0.2 mm to 1.5 mm, for example, and can be more preferably formed within a range from 0.3 mm to 0.7 mm. The inner diameter d2 of the vein side tubular member 140 after expanding deformation (i.e., radially outward expansion) can be preferably formed within a range from 0.2 mm to 1.5 mm, for example, and can be more preferably formed within a range from 0.3 mm to 0.7 mm.

Since a portion of the side wall 138 of the lymphatic vessel side tubular member 130 is cut and opened, the shape of the axially orthogonal cross section of the lymphatic vessel side tubular member 130 may not always be a perfect circle. For example, at the time of expanding deformation when the lymphatic vessel side tubular member is accommodated in the lumen 101 of the puncture member 100 or when the lymphatic vessel side tubular member is not yet fixed to the lymphatic vessel L, the axially orthogonal cross section shape of the lymphatic vessel side tubular member 140 may not be a perfect circle. Similarly, since a portion of the side wall 148 in the vein side tubular member 140 is cut and opened, the shape of the axially orthogonal cross section at the time of expanding deformation in a state of being accommodated in the lumen 101 of the puncture member 100 or not being fixed to the vein P may not be a perfect circle. In such cases, the outer dimensions of the side wall 138 (distance between the outer surfaces of the side wall 138) of the widest portion extending radially outward in the lymphatic vessel side tubular member 130 can be defined as the outer diameter d1, and the inner dimensions of the side wall 138 (distance between the inner surfaces of the side wall 148) of the widest portion extending radially outward in the vein side tubular member 140 can be defined as the inner diameter d2.

The dimensions (the length, the inner diameter when in the contracted state, the outer diameter, and the like) of other portions of the lymphatic vessel side tubular member 130, the dimensions (the length, the inner diameter when in the contracted state, the outer diameter, and the like) of other portions of the vein side tubular member 140, the outer shape of each of the tubular members 130, 140 before and after deformation, and the like are not particularly limited as long as the tubular members 130, 140 can be fixed to the body lumen.

As illustrated in FIGS. 3A and 3B, the lymphatic vessel side tubular member 130 is provided with a coming-off prevention portion 137 for preventing the lymphatic vessel side tubular member 130 from coming off from the puncture site t formed in the lymphatic vessel L.

The coming-off prevention portion 137 is configured to be a projection portion having a shape protruding radially outward from the side wall 138 (i.e., the outer diameter of the coming-off prevention portion 137 is greater than the outer diameter of the side wall 138). As illustrated in FIG. 10A, the coming-off prevention portion 137 is disposed on an inner surface L12b side of a tube wall L12 of the lymphatic vessel L when the lymphatic vessel side tubular member 130 has been inserted into the puncture site t formed in the lymphatic vessel L.

The coming-off prevention portion 137 causes the top surface of the coming-off prevention portion 137 to be attached to the inner surface L12b of the tube wall L12 of the lymphatic vessel L when force in a direction of coming out of the puncture site t (upward force in the FIG. 10A diagram) unexpectedly acts on the lymphatic vessel side tubular member 130. Due to the attachment or contact force between the top surface of the coming-off prevention portion 137 and the inner surface L12b of the tube wall L12 of the lymphatic vessel, the coming-off prevention portion 137 applies an engagement force that prevents the lymphatic vessel side tubular member 130 from coming off or out from the tube wall L12. In this manner, the coming-off prevention portion 137 in the lymphatic vessel side tubular member 130 more stably fixes the lymphatic vessel side tubular member 130 to the lymphatic vessel L.

For example, an expanding force, which acts on the lymphatic vessel L when the lymphatic vessel side tubular member 130 expands, can be set to have a magnitude to tightly fix the lymphatic vessel side tubular member 130 to the lymphatic vessel L while causing no damage to the lymphatic vessel L. Similarly, for example, an expanding force, which acts on the vein P when the vein side tubular member 140 expands, can be set to have a magnitude to tightly fix the vein side tubular member 140 to the vein P while causing no damage to the vein P.

In the present embodiment, the coming-off prevention portion 137 is integrally formed with the lymphatic vessel side tubular member 130 by adding a shape protruding radially outward to a portion of the lymphatic vessel side tubular member 130 (i.e., the coming-off prevention portion 137 is an integral component of the lymphatic vessel side tubular member 130). However, the coming-off prevention portion 137 can also be a separate member from the lymphatic vessel side tubular member 130 and be a different material than the lymphatic vessel side tubular member 130, for example, as described below in the modification examples and the like. Nevertheless, when the coming-off prevention portion 137 is a shape added to the lymphatic vessel side tubular member 130 as in the present embodiment, the coming-off prevention portion 137 can be easily manufactured and the structure of the lymphatic vessel side tubular member 130 can be simplified. Thus, it is possible to realize a simplified manufacturing process and a reduced manufacturing cost.

For example, as illustrated in FIGS. 3B and 10A, the coming-off prevention portion 137 can be formed to have a substantially triangular cross-sectional shape with the top surface side inclining toward the bottom surface side in a reverse-tapered manner and with the bottom surface side inclining toward the top surface side in a reverse-tapered manner (i.e., a point between the top surface side and the bottom surface side of the coming-off portion has a larger radial outer diameter than the top surface side and the bottom surface side to form a triangular cross-section with the top surface side and the bottom surface side). Since the coming-off prevention portion 137 is formed to have a substantially triangular cross-sectional shape, sliding resistance between the coming-off prevention portion 137 and the inner surface of the puncture member 100 can be reduced when the lymphatic vessel side tubular member 130 moves inside the lumen 101 of the puncture member 100. It is thus possible to smoothly move the lymphatic vessel side tubular member 130 within the lumen 101 of the puncture member 100. The cross-sectional shape of the coming-off prevention portion 137 is not limited to the illustrated shape and can be appropriately changed. The protrusion length extending radially outward (dimensions of the protruding portion) at the time of expanding deformation of the lymphatic vessel side tubular member 130, the position to be provided in the lymphatic vessel side tubular member 130, and the like are not particularly limited, and can also be appropriately changed.

As described above, the lymphatic vessel side tubular member 130 is fixed to the puncture site t by causing expanding deformation force (i.e., a pressing force) to act on the puncture site t at the time of expanding deformation. The lymphatic vessel side tubular member 130 can have self-expandability, for example, for self-expanding in accordance with the release from the puncture member 100 so as to be able to perform fixing by utilizing such an expanding force.

As a method of causing the lymphatic vessel side tubular member 130 to have self-expandability, for example, a portion or the entirety of the lymphatic vessel side tubular member 130 could be made from a material having a self-expandability. In the present embodiment, the lymphatic vessel side tubular member 130 is made from a self-expandable material so that the lymphatic vessel side tubular member 130 possesses the fixing function (i.e., the lymphatic vessel side tubular member 130 is configured to expand to fix the lymphatic vessel side tubular member 130 in the puncture site t of the lymphatic vessel L).

Examples of materials having self-expandability include a shape memory polymer, a shape memory alloy, and a super-elastic alloy. As the shape memory polymer, for example, it is possible to use an acrylic resin, a trans-isoprene polymer, polynorbornene, a styrene-butadiene copolymer, and polyurethane. As the shape memory alloy and the super-elastic alloy, for example, it is possible to use a titanium-based alloy (Ti—Ni, Ti—Pd, Ti—Nb—Sn, and the like), a copper-based alloy, stainless steel (SUS 304), β titanium steel, a Co—Cr alloy, and an alloy such as a nickel-titanium alloy having spring characteristics.

As long as the lymphatic vessel side tubular member 130 can be accommodated inside of the lumen 101 of the puncture member 100 and can perform the expanding deformation when being released from the lumen 101 so as to be fixed to the puncture site t, the entirety of the lymphatic vessel side tubular member 130 does not necessarily need to be configured to perform expanding deformation and contracting deformation. For example, the lymphatic vessel side tubular member 130 may be partially configured to perform expanding deformation and contracting deformation.

Similar to the lymphatic vessel side tubular member 130, for example, the vein side tubular member 140 can be made from a self-expanding material so as to have a fixing function for performing fixing with respect to the vein P (i.e., to fix the vein side tubular member 140 in the vein P). Examples of self-expandable materials include similar materials discussed above for the lymphatic vessel side tubular member 130. Similar to the lymphatic vessel side tubular member 130, as long as the vein side tubular member 140 can be accommodated inside the lumen 101 of the puncture member 100 and can be fixed to the vein P due to expanding deformation performed in accordance with the release from the lumen 101, the entirety of the vein side tubular member 140 does not necessarily need to be able to perform expanding deformation and contracting deformation. For example, the vein side tubular member 140 may be partially configured to perform expanding deformation and contracting deformation.

The lymphatic vessel side tubular member 130 and the vein side tubular member 140 can be provided with a structure for regulating an interlocking position, for example, when interlocking both the members with each other. As an example, an uneven fitting portion is provided on the outer surface of the lymphatic vessel side tubular member 130 and an uneven fitting portion, which is freely fitted into the fitting portion, is provided on the inner surface of the vein side tubular member 140. It is thus possible to employ a structure to regulate the interlocking position via the fitting portions by inserting the vein side tubular member 140 into the lymphatic vessel side tubular member 130. Alternatively, it is possible to regulate the interlocking position by providing magnets or the like in the lymphatic vessel side tubular member 130 and the vein side tubular member 140 to cause magnetic force to act to control the interlocking position. When the fitting portions, the magnets, or the like are provided, the fixing force (i.e., the interlocking force) between the lymphatic vessel side tubular member 130 and the vein side tubular member 140 may be increased. In addition, surface treatment for enhancing the friction force may be applied so that the lymphatic vessel side tubular member 130 and the vein side tubular member 140 are not easily separated from one another after being interlocked. A combination of a structure for regulating the interlocking position and enhancing the friction force with a surface treatment could be used. One example is a reversal structure on the outer surface of the lymphatic vessel side tubular member 130 to be obliquely higher from the proximal side to the distal side and a recessed structure on the inner surface of the vein side tubular member 140 to be able to hook in the reversal structure, and an anti-slipping coating such as urethane coating being applied to enhance the friction force between the lymphatic vessel side tubular member 130 and the vein side tubular member 140. However, the surface treatment is not limited to urethane coating.

For another example, the lymphatic vessel side tubular member 130 can be provided with a seal portion that prevents lymph from flowing out from between the side wall 138 of the lymphatic vessel side tubular member 130 and the puncture site t when the lymphatic vessel side tubular member 130 is inserted into the puncture site t of the lymphatic vessel L. The seal portion, for example, can be a biocompatible gel or the like which swells when in contact with a body fluid (e.g., lymph) so that the seal portion fixedly adheres to the side wall 138 of the lymphatic vessel side tubular member 130.

Since blood or a lymphatic fluid comes into contact with the inner surface and the outer surface of each of the tubular members 130, 140 when the tubular members 130, 140 indwell in the body lumen (e.g., the lymphatic vessel L, the vein P), it is preferable to apply various types of coating or the like to each of the tubular members 130, 140.

For example, an antithrombotic substance can be mixed into the material of each of the tubular members 130, 140, or each of the tubular members 130, 140 can be coated with an antithrombotic substance. Particularly, since it is highly possible that the vein side tubular member 140 comes into contact with blood in the vein P, it is preferable to apply antithrombotic characteristics to the outer surface of the vein side tubular member 140 in order to prevent thrombus and the like from adhering to the outer surface of the vein side tubular member 140.

Examples of the above-described antithrombotic material include heparin, a heparin-like substance, PMEA (poly (2-methoxy-ethyl acrylate)), PEG (polyethylene glycol), a betaine zwitterionic polymer, and the like.

When each of the tubular members 130, 140 is used to join the lymphatic vessel L and the vein P together for treating lymphedema, a lymphatic fluid flows into the vein P side due to the pressure difference between the lymphatic vessel L and the vein P. Since protein concentration of the lymphatic fluid is extremely high, when a great quantity of the protein is adsorbed onto the inner surface of each of the tubular members 130, 140, there is a clogging possibility for each of the tubular members 130, 140. Therefore, it is preferable that the inner surface of each of the tubular members 130, 140 be an adhesion preventing surface with coating or the like for preventing protein and the like from adhering to the inner surface of the tubular member 130, 140.

For example, the adhesion preventing surface can have a hydrophilic coating, a fluorine-based coating, a silicon-based coating, a micro-uneven structure, a combination of the above-referenced coating and the uneven structure, a stable liquid phase such as silicon oil and fluorine-based oil which are not mixed with blood retained on the surface, or the like at an arbitrary place in each of the tubular members 130, 140.

As illustrated in FIG. 2, the outer tube 170 provided in the medical apparatus 10 is a hollow member including a lumen 171 that accommodates a portion of the distal side of the puncture member 100, a distal opening portion 173 at the distal end of the lumen 171, and a proximal opening portion 175 at the proximal end of the lumen 171.

The negative pressure generation member 180 includes a rod-like main body portion 181 which is capable of being inserted into the lumen 101 of the puncture member 100 (i.e., the rod-like main body portion 181 is movable relative to the lumen 101), a valve body (plunger) 183 at the distal end of the main body portion 181, a seal member 183a for ensuring airtight characteristics between the negative pressure generation member 180 and an inner wall of the puncture member 100, a finger hook portion 185a for a user to grasp, hook their fingers or the like when operating the negative pressure generation member 180, an insertion-though hole 181a through which the main body portion 151 of the plunger 150 is inserted, and a proximal opening portion 185 to which the main body portion 151 of the plunger 150 is led out (i.e., the main body portion 151 of the plunger 150 passes through and proximally beyond the proximal opening portion 185). The valve body 183 of the negative pressure generation member 180 is slidably inserted into the lumen 101 of the puncture member 100.

As illustrated in FIG. 6A, when the negative pressure generation member 180 is used, an airtight space portion g is created around the puncture member 100 by causing the outer tube 170 to cover the outer circumferential surface of the puncture member 100, disposing the distal opening portion 173 of the outer tube 170 to contact an outer surface L12a of the tube wall L12 of the lymphatic vessel L, and closing the distal opening portion 173.

When the space portion g is created by the outer tube 170, and the valve body 183 of the negative pressure generation member 180 is slid (i.e., retracted) toward the proximal side of the puncture member 100 as illustrated in FIG. 6B, suctioning pressure acts on the space portion g via the distal opening portion 103 of the puncture member 100. Negative pressure is thus generated inside the space portion g. Accordingly, the tube wall L12 of the lymphatic vessel L lifts, and the tube wall L12 displaces to approach the needle tip 107 of the puncture member 100 (i.e., the tube wall L12 is pulled closer to the needle tip 107). When the tube wall L12 displaces, the distance between a needle-insertion target position b in the tube wall L12 at which the needle tip 107 of the puncture member 100 is inserted and a bottom surface L12c of the tube wall L12 is in a widened state (i.e., it is farther from the needle tip 107 to the bottom surface L12c than it is when the tube wall L12 does not displace towards the needle tip 107). It is thus possible to favorably prevent the needle tip 107 from reaching the bottom surface L12c of the tube wall L12 when the puncture member 100 punctures the lymphatic vessel L in the above-described state.

Since the needle tip 107 of the puncture member 100 can be inserted due to the action of suctioning pressure in a state where the needle-insertion target position b is captured, the needle tip 107 can be easily introduced toward the needle-insertion target position b. It is thus possible to prevent the needle tip 107 from unintentional puncturing while deviating from the needle-insertion target position b. Moreover, since puncturing is performed in a state where the surroundings of a swelling portion (the lifted portion) L13 of the tube wall L12 are protected by being covered with the outer tube 170, the puncture site t (which is formed as a result of puncturing) can be protected by the outer tube 170 immediately after puncturing. In this manner, the puncture site t can be maintained in a clean state, and it is possible to prevent damage and the like to the puncture site t and the peripheral sites occurring due to the influence of surrounding environment while performing the technique.

As illustrated in FIG. 6B, a through hole 153*a* penetrating the push-in portion 153 in the axial direction is formed in the push-in portion 153 of the plunger 150. The push-in portion 153 of the plunger 150 is disposed on the distal side of the valve body 183 when negative pressure is generated in the space portion g so that suctioning action as a result of sliding of the valve body 183 is not hindered.

It is preferable that the negative pressure generation member 180 is made from an elastically deformable resin material to retain airtight characteristics with respect to the inner surface of the puncture member 100 and with respect to the plunger 150 which is inserted through the insertion-though hole 181*a*. Forming the negative pressure generation member 180 from an elastically deformable resin material also allows the negative pressure generation member 180 to be able to slide in the lumen 101 of the puncture member 100. Examples of resin materials include natural rubber, butyl rubber, isoprene rubber, butadiene rubber, styrene-butadiene rubber, styrene-ethylene-butylene styrene rubber, ethylene propylene rubber, acrylonitrile-butadiene rubber, fluorine rubber, urethane rubber, polysulfide rubber, chlorinated butyl rubber, silicone rubber, and the like.

As illustrated in FIG. 2, the medical apparatus 10 can be prepared by integrally assembling the lymphatic vessel side tubular member 130, the vein side tubular member 140, the puncture member 100, the plunger 150, the outer tube 170, and the negative pressure generation member 180.

The puncture member 100 is inserted (i.e., distally moved) into the lumen 171 of the outer tube 170 while accommodating the lymphatic vessel side tubular member 130 and the vein side tubular member 140. The outer tube 170 is assembled to be slidable relative to the puncture member 100. The plunger 150 is inserted (i.e., distally moved) into the insertion-though hole 181*a* of the negative pressure generation member 180. The plunger 150 is assembled to be slidable relative to the negative pressure generation member 180.

When the medical apparatus 10 is assembled as illustrated in FIG. 2, the proximal portion of the puncture member 100 can be positioned to be exposed from the proximal opening portion 175 of the outer tube 170 by a predetermined length (i.e., a predetermined length of the puncture member 100 extends proximally beyond the proximal opening portion 175 of the outer tube). As a result of such a positioning, the puncture member 100 can be operated by grasping the proximal portion of the puncture member 100 with fingers and the like allowing a user to move the puncture member 100.

The proximal portion of the main body portion 181 of the negative pressure generation member 180 can be disposed to be exposed from the proximal opening portion 105 of the puncture member 100 by a predetermined length (i.e., a predetermined length of the proximal portion of the main body portion 181 of the negative pressure generation member 180 extends proximally beyond the proximal opening portion 105 of the puncture member 100). The proximal portion of the main body portion 151 of the plunger 150 can be disposed so as to be exposed from the proximal opening portion 185 of the negative pressure generation member 180 by a predetermined length (i.e., a predetermined length of the proximal portion of the main body portion 151 extends proximally beyond the proximal opening portion 185 of the negative pressure generation member). As a result of such positioning, the negative pressure generation member 180 can be operated by grasping the proximal portion of the main body portion 181 with fingers and the like when moving the negative pressure generation member 180. In addition, the plunger 150 can be operated by grasping the proximal portion of the main body portion 151 with fingers and the like when moving the plunger 150.

As illustrated in FIG. 2, the puncture member 100 is provided with a stopper 108 which regulates a needle-insertion amount (depth of needle-insertion) of the needle tip 107 when the needle tip 107 of the puncture member 100 is inserted into the tube wall L12 of the lymphatic vessel L. The stopper 108 is a ring-like member attached to an outer circumferential portion in the vicinity of the proximal portion of the puncture member 100.

As illustrated in FIG. 7B, when the needle tip 107 of the puncture member 100 is inserted into the tube wall L12 of the lymphatic vessel L and the puncture member 100 moves forward to the distal side by a predetermined distance with respect to the outer tube 170, the stopper 108 is attached to a proximal end wall 175*a* of the outer tube 170. After the stopper 108 is attached to the proximal end wall 175*a* of the outer tube 170, moving forward of the puncture member 100 is regulated (i.e., further distal movement is prevented). Accordingly, the needle tip 107 of the puncture member 100 is also regulated from entering the inside of the lymphatic vessel L (i.e., further distal movement is prevented). In this manner, it is possible to favorably prevent the needle tip 107 from reaching the bottom surface L12*c* of the tube wall L12 by providing the stopper 108. Therefore, it is possible to realize the safer technique.

A use example of the medical apparatus 10 according to the present embodiment is described below.

Here, description is provided regarding an example of using the medical apparatus 10 in side-to-end anastomosis in which an opening end P31 of the vein P is joined to the tube wall L12 of the lymphatic vessel L.

With reference to FIG. 4, a method of treating lymphedema generally includes step S11 of specifying (i.e., identifying) a lymphatic vessel as the joining target (specifying step), step S12 of exposing the lymphatic vessel and a vein by performing incision of the skin (exposing step), step S13 of expanding the lymphatic vessel (expanding step), step S14 of fixing the lymphatic vessel side tubular member to the lymphatic vessel (first fixing step), step S15 of fixing the vein side tubular member to the vein (second fixing step), and step S16 of joining the lymphatic vessel and the vein together by interlocking the lymphatic vessel side tubular member and the vein side tubular member with each other (joining step). Each of the steps is described in greater detail below.

First, the specifying step (S11) is performed.

In the specifying step (311), a user specifies (i.e., identifies) a lymphatic vessel L as the joining target. For example, indocyanine green (ICG) fluorescence lymphangiography can be used for specifying the lymphatic vessel L. FIG. 5A schematically illustrates a state where the lymphatic vessel L is visualized by performing the ICG fluorescence lymphangiography.

In the ICG fluorescence lymphangiography, an ICG contrast agent is injected into several places on an arm or a leg having a target lesion, thereby visualizing a flow inside the lymphatic vessel by using a known infrared camera. An arbitrary lymphatic vessel L is then specified as the joining target, among the lymphatic vessels L in which the flow of the ICG contrast agent is congested. For example, when treating lymphedema on a leg, a lymphatic vessel existing in the dorsum of a foot, the ankle, the lower thigh, above the knee, below the knee, or the like can be selected as the joining target. When treating lymphedema on an arm, a lymphatic vessel existing in the periphery of the wrist, the forearm, the periphery of the elbow, or the like can be selected as the joining target. Moreover, it is possible to select a shallow lymphatic vessel which exists immediately under a skin S as the lymphatic vessel.

Subsequently, the exposing step (S12) is performed.

In the exposing step (S12), as illustrated in FIG. 5B, an incision site d is formed by performing incision of the skin S covering the lymphatic vessel L as the joining target, thereby exposing the lymphatic vessel L (i.e., an area of the skin S covering the lymphatic vessel L is cut). The incision can be performed by using a known treatment tool such as a scalpel.

Subsequently, the expanding step (S13) is performed.

In the expanding step (S13), as illustrated in FIG. 5C, while a portion La on the upstream side of the flow of lymph is clamped, the lymphatic vessel L is expanded by stimulating the lymphatic vessel L. For example, the lymphatic vessel L having the outer diameter of 0.45 mm can be expanded in the expanding step (S13) to have an outer diameter of 0.70 mm. Since the lymphatic vessel L becomes easier to handle in the following steps by expanding the lymphatic vessel L than when the lymphatic vessel L is not expanded, it is possible to realize an easier and expedited technique.

In the expanding step (S13), for example, the surface of the lymphatic vessel L is massaged by causing a predetermined auxiliary tool 220 to reciprocate from the portion La on the upstream side of the flow of lymph to a portion Lb on the downstream side of the flow of lymph (i.e., the auxiliary tool 220 alternates between massaging the portion La on the upstream side and the portion Lb on the downstream side of the flow of lymph). For example, small forceps or the like which is used in microsurgery and the like can be used as an auxiliary tool 210 for clamping the lymphatic vessel L, and as the auxiliary tool 220 for massaging the lymphatic vessel L.

The first fixing step (S14) can be executed by using the medical apparatus 10.

When starting the first fixing step (S14), as illustrated in FIG. 2, the medical apparatus 10 is prepared with the lymphatic vessel side tubular member 130, the vein side tubular member 140, the puncture member 100, the plunger 150, the outer tube 170, and the negative pressure generation member 180 integrally assembled.

Subsequently, as illustrated in FIG. 6A, the distal portion of the outer tube 170 is moved to contact the outer surface L12a of the tube wall L12 of the lymphatic vessel L. When the distal portion of the outer tube 170 contacts the outer surface L12a of the tube wall L12 of the lymphatic vessel L, a space portion g is formed within the outer tube 170.

Subsequently, as illustrated in FIG. 6B, the negative pressure generation member 180 of the medical apparatus 10 is moved to the proximal side (i.e., the negative pressure generation member 180 is moves in the proximal direction), thereby generating negative pressure inside the space portion g. A portion of the tube wall L12 of the lymphatic vessel L lifts. This operation forms a swelling portion L13 in the tube wall L12 of the lymphatic vessel L.

Subsequently, as illustrated in FIG. 7A, the puncture member 100 is moved to the distal side so that the needle tip 107 punctures the swelling portion L13 of the lymphatic vessel L. The puncture site (puncture hole) t is formed in the tube wall L12 by the needle tip's 107 penetration of the tube wall L12.

Subsequently, as illustrated in FIG. 7B, the plunger 150 is moved distally (i.e., the plunger is pushed forward towards the distal opening portion 103), the vein side tubular member 140 is pushed towards the distal opening portion 103, and the lymphatic vessel side tubular member 130 positioned on the distal side of the vein side tubular member 140 is pushed towards the distal opening portion 103. The lymphatic vessel side tubular member 130 is moved distally to the inner side of the puncture site t through this operation. In this case, the coming-off prevention portion 137 of the lymphatic vessel side tubular member 130 is disposed on the inner side of the lymphatic vessel L closer than the inner surface L12b of the tube wall L12 of the lymphatic vessel L (i.e., the coming-off prevention portion 137 of the lymphatic vessel side tubular member is moved distally to be within the lymphatic vessel L).

Subsequently, as illustrated in FIG. 8A, the lymphatic vessel side tubular member 130 is released from the distal opening portion 103 of the puncture member 100 by moving the puncture member 100 to the proximal side and moving the plunger 150 to the distal side (i.e., the puncture member 100 moves proximally and the plunger 150 moves distally).

As illustrated in FIG. 8B, the lymphatic vessel side tubular member 130 performs expanding deformation radially outward (i.e., expands radially outward) in accordance with the release from the distal opening portion 103 of the puncture member 100. When the lymphatic vessel side tubular member 130 expands radially outward, the side wall 138 presses against the inner surface of the puncture site t. The lymphatic vessel side tubular member 130 maintains a state of being fixed to the lymphatic vessel L by causing expanding deformation force to continuously act on the puncture site t (i.e., the expanding force of the lymphatic vessel side tubular member 130 holds/fixes the lymphatic vessel side tubular member 130 at the puncture site t).

After fixing the lymphatic vessel side tubular member 130 to the lymphatic vessel L, the puncture member 100 is moved in the proximal direction so as to retreat (i.e., retract) from the lymphatic vessel L. As illustrated in FIG. 8B, when the puncture member 100 moves proximally a flow of lymph is induced from a lumen L11 of the lymphatic vessel L into the space portion g. This occurs because the space portion g defined by the outer tube 170 communicates with the lumen L11 of the lymphatic vessel L via the lymphatic vessel side tubular member 130, and because of the pressure difference between pressure inside the space portion g and pressure inside the lumen L11 of the lymphatic vessel L. Accordingly, it is possible to promote the congested flow of lymph inside the lymphatic vessel L (i.e., the congestion can be reduced).

When lymph is allowed to flow into the space portion g, the number of steps of the technique increases due to the need for removing lymph from the space portion g. In order to prevent the number of such steps from increasing, for example, the outer tube 170 can be provided with a leak valve for exposing the space portion g to the atmosphere. Since an operation of restoring the pressure inside the space portion g to the atmosphere can be performed by providing the leak valve, before causing the space portion g and the lumen L11 to communicate with each other, it is possible to prevent the occurrence of the above-described flow of lymph leading to the space portion g.

The swelling portion L13 formed in the lymphatic vessel L vanishes as the space portion g defined by the outer tube 170 is exposed to the atmosphere (i.e., the induced swelling goes away in the tube wall L12 of the lymphatic vessel L).

As illustrated in FIG. 9A, after ending the first fixing step (S14) of fixing the lymphatic vessel side tubular member 130 to the lymphatic vessel L, the entirety of the medical apparatus 10 is moved to retreat from the lymphatic vessel L.

After ending the first fixing step (S14), the lymphatic vessel side tubular member 130 indwells in the lymphatic vessel L with the distal portion of the lymphatic vessel side tubular member 130 inserted into the lumen L11 of the lymphatic vessel L and with the proximal portion of the lymphatic vessel side tubular member exposed from the lumen L11 of the lymphatic vessel L.

Subsequently, the second fixing step (S15) is performed.

The second fixing step (S15) can be executed by using the medical apparatus 10.

First, as illustrated in FIG. 9B, the distal portion of the puncture member 100 is inserted into the lumen P11 of the vein P which becomes the joining target. In this case, for example, the position of the vein side tubular member 140 is adjusted so that the proximal opening portion 145 of the vein side tubular member 140 is disposed in the vicinity of the opening end P31 of the vein P.

The vein P which becomes the joining target can be appropriately selected from veins which exist in the vicinity of the lymphatic vessel L. In addition, the opening end P31 can be formed in advance by cutting the vein P before the vein side tubular member 140 is inserted into the lumen P11. The opening end P31 is a joint between the vein P and the lymphatic vessel L in this embodiment.

Subsequently, as illustrated in FIG. 9B, the vein side tubular member 140 is released into the lumen P11 of the vein P via the distal opening portion 103 of the puncture member 100 by moving the puncture member 100 to the proximal side and moving the plunger 150 to the distal side (i.e., the puncture member 100 moves proximally and the plunger 150 moves distally to release the vein side tubular member 140).

As illustrated in FIG. 10A, the vein side tubular member 140 performs expanding deformation radially outward (i.e., expands radially outward) in accordance with the release from the lumen 101 of the puncture member 100. When the vein side tubular member 140 expands radially outward, the side wall 148 of the vein side tubular member 140 presses against the inner surface of the vein P. The vein side tubular member 140 maintains a state of being fixed to the vein P by causing expanding deformation force to continuously act on the inner surface of the vein P (i.e., the expanding force of the vein side tubular member 140 holds/fixes the vein side tubular member 140 in the vein P).

In the present embodiment, when starting the technique, the medical apparatus 10 is prepared with the lymphatic vessel side tubular member 130 in the lumen 101 of the puncture member 100 and the vein side tubular member 140 in the lumen 101 of the puncture member 100 on the proximal side, more proximal than the position at which the lymphatic vessel side tubular member 130 is accommodated (refer to FIG. 2). Therefore, after ending the first fixing step (S14) of fixing the lymphatic vessel side tubular member 130 to the lymphatic vessel L, the second fixing step (S15) of fixing the vein side tubular member 140 to the vein P can be successively executed by using the medical apparatus 10.

After ending the second fixing step (S15) of fixing the vein side tubular member 140 to the vein P, the joining step (S16) is executed.

As illustrated in FIG. 10B, in the joining step (S16), the lymphatic vessel side tubular member 130 and the vein side tubular member 140 are interlocked with each other.

For example, the interlocking is performed by causing the opening end P31 side on which the vein side tubular member 140 is disposed in the vein P to approach the lymphatic vessel side tubular member 130 which is fixed to the lymphatic vessel L. In this case, the proximal portion of the lymphatic vessel side tubular member 130, which is exposed from the tube wall L12 of the lymphatic vessel L, is inserted into the lumen 141 of the vein side tubular member 140. As a result of this movement, the lymphatic vessel side tubular member 130 and the vein side tubular member 140 are mechanically interlocked with each other, and the lymphatic vessel L and the vein P are joined together.

For example, the joining work of the lymphatic vessel L and the vein P is performed by fixing the position of the lymphatic vessel L using small forceps or the like which is used in microsurgery and the like and causing the vein P which is grasped by using the small forceps or the like to approach the lymphatic vessel L (i.e., a user uses a tool such as forceps to move and then join the lymphatic vessel L and the vein P).

When the lymphatic vessel L and the vein P are joined together, a flow path of lymph leading from the lymphatic vessel L to the vein P is formed by the lumen L11 of the lymphatic vessel L, the lumen 131 of the lymphatic vessel side tubular member 130, the lumen 141 of the vein side tubular member 140, and the lumen P11 of the vein P.

Generally, pressure inside the lymphatic vessel L (lymphatic pressure) of a patient who is affected by lymphedema is higher than pressure inside the vein P (venous pressure). This higher pressure inside the lymphatic vessel L is due to the congested flow of lymph. Therefore, when the lymphatic vessel L and the vein P are joined together, a flow path of lymph from the lymphatic vessel L side to the vein P side is induced in a relatively easy manner. As a result of creating this flow path of lymph, accumulation of lymph causing lymphedema is resolved, and thus, symptoms such as edema at the target lesion are alleviated.

When the side-to-end anastomosis described in the present embodiment is performed, a flow path of lymph is formed leading from the upstream La side of the lymphatic vessel L to the vein P and a flow path of lymph is formed leading from the downstream Lb side of the lymphatic vessel L to the vein P. Therefore, it is possible to efficiently resolve the accumulated lymph causing lymphedema.

When being affected by lymphedema, the function of a valve existing inside the lymphatic vessel L declines so that backflow of lymph continuously occurs inside the lymphatic vessel L. Therefore, after the side-to-end anastomosis is performed, a flow from the upstream La side of the lymphatic vessel L and a flow from the downstream Lb side of the lymphatic vessel L are easily induced. Moreover, before and after the side-to-end anastomosis is performed, a flow from the downstream Lb side of the lymphatic vessel L is retained. There is thus no sudden change of the flow of lymph after the side-to-end anastomosis is performed, and it is possible to favorably prevent an excessive load applied to the lymphatic vessel L.

After joining a specified lymphatic vessel L and a specified vein P together, procedures of joining a different lymphatic vessel L and a different vein P together can be successively executed. In this manner, the site in which the lymphatic vessel L and the vein P are joined together can be formed at a plurality of places in one patient.

The method of treating lymphedema according to the present embodiment described above includes a step of joining (bypass operation) the lymphatic vessel L and the vein P via the tubular members 130, 140.

The method of treating lymphedema includes a side-to-end joining step (side-to-end anastomosis step) of joining the tube wall L12 of the lymphatic vessel L and the opening end P31 of the vein P together via the tubular member 130 fixed to the tube wall L12 of the lymphatic vessel L and the tubular member 140 fixed to the opening end P31 of the vein P.

The method of treating lymphedema also includes a step of forming a puncture site by puncturing the tube wall of the lymphatic vessel; a step of inserting and fixing the lymphatic vessel side tubular member, which can perform expanding deformation, with respect to the puncture site; a step of inserting and fixing the vein side tubular member, which can perform expanding deformation, with respect to the opening end of the vein; and a step of joining the lymphatic vessel and the vein performed by interlocking the lymphatic vessel side tubular member and the vein side tubular member with each other.

The method of treating lymphedema also includes a step of forming a swelling portion, which is displaced to the needle tip side of the puncture member, in a portion of the tube wall of the lymphatic vessel when forming the puncture site in the tube wall of the lymphatic vessel; and inserting the needle tip of the puncture member into the swelling portion.

The method of treating lymphedema also includes a step of specifying the lymphatic vessel which becomes the joining target before the step of joining the lymphatic vessel and the vein via the tubular member, a step of exposing the lymphatic vessel and the vein by performing incision of the skin, and a step of expanding the lymphatic vessel.

As described above, the medical apparatus 10 according to the present embodiment includes the puncture member 100 that includes the lumen 101 and the distal opening portion 103 at the distal end of the lumen 101. The distal end of the puncture member 100 includes the needle tip 107 that forms the puncture site t by puncturing the tube wall L12 of the lymphatic vessel L, the lymphatic vessel side tubular member 130 that is accommodated in the lumen 101 of the puncture member 100 and is configured to be able to perform expanding deformation radially outward (i.e., expand radially outward) and to perform contracting deformation (i.e., contract radially inward), and the plunger 150 that is movably inserted into the lumen 101 of the puncture member 100 and releases the lymphatic vessel side tubular member 130 from the distal opening portion 103 of the puncture member 100 in accordance with relative movement with respect to the puncture member 100. The lymphatic vessel side tubular member 130 is accommodated in the lumen 101 of the puncture member 100 in the contracted state and performs the expanding deformation in accordance with the release from the distal opening portion 103 of the puncture member 100 so as to be fixed to the puncture site t.

According to the medical apparatus 10 having the above-described configuration, a flow of lymph (lymphatic fluid) leading from the lymphatic vessel L to the vein P can be formed by fixing the lymphatic vessel side tubular member 130 to the puncture site t (which is formed by causing the needle tip 107 of the puncture member 100 to puncture the lymphatic vessel L), and joining the lymphatic vessel L and the vein P together via the lymphatic vessel side tubular member 130. The lymphatic vessel side tubular member 130 which can expand and contract is used as a member to join the lymphatic vessel L and the vein P together. Accordingly, it is possible to smoothly indwell the lymphatic vessel side tubular member 130 in the puncture site t in a lymphatic vessel L that has a relatively small diameter. Moreover, there is no need to form the minute window portion in the lymphatic vessel L by performing procedures of incision or the like as that in lymphaticovenular anastomosis in the related art. Accordingly, it is possible to promptly and easily perform the procedure and it is possible to drastically shorten time taken for the procedure.

The medical apparatus 10 also includes the outer tube 170 that is disposed to cover the outer circumferential surface of the puncture member 100 and defines the space portion g between the puncture member 100 and the tube wall L12 of the lymphatic vessel L when the needle tip 107 punctures the tube wall L12 of the lymphatic vessel L, and the negative pressure generation member 180 that causes the tube wall L12 of the lymphatic vessel L to be displaced toward (i.e., be pulled towards) the needle tip 107 of the puncture member 100 by generating negative pressure in the space portion g. Accordingly, when causing the needle tip 107 of the puncture member 100 to puncture the tube wall L12 of the lymphatic vessel L, the tube wall L12 can be displaced so as to approach the needle tip 107 of the puncture member 100. Accordingly, it is possible to favorably prevent the needle tip 107 from reaching the bottom surface L12c of the tube wall L12. Therefore, it is possible to realize the safer technique.

The negative pressure generation member 180 has the valve body 183 which causes suctioning pressure to act on the space portion g via the distal opening portion 103 of the puncture member 100 by being slidably inserted into the lumen 101 (i.e., movable within the lumen 101) of the puncture member 100 and sliding toward the proximal side of the puncture member 100. Accordingly, it is possible to generate negative pressure in the space portion g by sliding the valve body 183 through a user's operation.

The lymphatic vessel side tubular member 130 has the coming-off prevention portion 137 which causes engagement force that prevents the lymphatic vessel side tubular member 130 from coming off from the puncture site t to act on the tube wall L12 of the lymphatic vessel L. Accordingly, it is possible to more stably maintain a state where the lymphatic vessel side tubular member 130 is fixed to the lymphatic vessel L.

The medical apparatus 10 includes the vein side tubular member 140 that is accommodated on the proximal side closer to the operator than a position where the lymphatic vessel side tubular member 130 is accommodated in the lumen 101 of the puncture member 100 (i.e., the vein side tubular member is proximal to the lymphatic side tubular member). The vein side tubular member is configured to be able to perform expanding deformation radially outward (i.e., expand radially outward) and to perform contracting deformation (i.e., contract radially inward), and is configured to be able to be interlocked with the lymphatic vessel side tubular member 130. Accordingly, it is possible to promptly and easily join the lymphatic vessel L and the vein P together via the lymphatic vessel side tubular member 130 and the vein side tubular member 140. Moreover, after ending procedures of fixing the lymphatic vessel side tubular member 130 to the lymphatic vessel L, procedures of fixing the vein side tubular member 140 to the vein P can be successively executed by using the medical apparatus 10. Accordingly, it is possible to more promptly perform the procedure using the two tubular members 130 and 140.

The diameter (inner diameter) d2 of the lumen 141 of the vein side tubular member 140 after expanding deformation is formed to be greater than the outer diameter d1 of the lymphatic vessel side tubular member 130 after expanding deformation. Accordingly, when the lymphatic vessel side tubular member 130 is inserted into the lumen 141 of the vein side tubular member 140 and the lymphatic vessel L and the vein P are joined together, the tube wall P12 of the vein P can be prevented from being pinched between the lymphatic vessel side tubular member 130 and the vein side tubular member 140. Therefore, it is possible to smoothly interlock the lymphatic vessel side tubular member 130 and the vein side tubular member 140 with each other.

Subsequently, with reference to FIGS. 11A to 13B, the below description includes deformation examples of a technique using the tubular members (the lymphatic vessel side tubular member 130 and the vein side tubular member 140). In the below descriptions of each deformation example, a procedure of using the medical apparatus 10, a configuration of the medical apparatus 10, and the like, any description already explained above in regards to the above-described embodiment will be omitted. In the description of each deformation example, description of a similar procedure, a similar configuration, and the like will be appropriately omitted.

Deformation Example 1

FIGS. 11A and 11B illustrate end-to-side anastomosis in which an opening end L31 of the lymphatic vessel L and the tube wall P12 of the vein P are joined together by using a lymphatic vessel side tubular member 330 and a vein side tubular member 340.

In the above-described side-to-end anastomosis, the tube wall L12 of the lymphatic vessel L and the opening end P31 of the vein P are joined together by interlocking the lymphatic vessel side tubular member 130 (which is fixed to the puncture site t formed in the tube wall L12 of the lymphatic vessel L) and the vein side tubular member 140 (which is fixed to the vicinity of the opening end P31 of the vein P) with each other. In the end-to-side anastomosis according to the present deformation example, as illustrated in FIGS. 11A and 11B, the opening end L31 of the lymphatic vessel L and the tube wall P12 of the vein P are joined together by interlocking the lymphatic vessel side tubular member 330 (which is fixed to the vicinity of the opening end L31 of the lymphatic vessel L) and the vein side tubular member 340 (which is fixed to the puncture site t formed in the tube wall P12 of the vein P) with each other.

The end-to-side anastomosis according to the present deformation example can be performed by using the medical apparatus 10. Specifically, the procedure is performed through the following process.

First, the puncture site t is formed in the tube wall P12 of the vein P by using the puncture member 100, and the vein side tubular member 340 is fixed to the puncture site t. This step can be performed through the procedure similar to the first fixing step (S14) in the above-described embodiment.

Subsequently, the lymphatic vessel side tubular member 330 is fixed to the vicinity of the opening end L31 of the lymphatic vessel L by using the puncture member 100. This step can be performed through the procedure similar to the second fixing step (S15) in the above-described embodiment.

Subsequently, a portion exposed from the tube wall P12 of the vein P in the vein side tubular member 340 is inserted into the lumen of the lymphatic vessel side tubular member 330. The lymphatic vessel side tubular member 330 and the vein side tubular member 340 are thus mechanically interlocked with one another, and so the lymphatic vessel L and the vein P are joined together. This step can be performed through the procedure similar to the joining step (S16) in the above-described embodiment.

When the end-to-side anastomosis according to the present deformation example is performed, similar to a case of performing the side-to-end anastomosis, a flow path of lymph is formed from the lymphatic vessel L side to the vein P side. Accordingly, it is possible to resolve accumulation of lymph causing lymphedema.

A tubular member having a configuration similar to the vein side tubular member 140 described in the above-referenced embodiment may be used as the lymphatic vessel side tubular member 330. A tubular member (provided with a coming-off prevention portion 347) having a configuration similar to the lymphatic vessel side tubular member 130 described in the above-referenced embodiment may be used as the vein side tubular member 340. When using the puncture member 100, the lymphatic vessel side tubular member 330 is fixed to the lymphatic vessel L after the vein side tubular member 340 is fixed to the vein P. Therefore, it is preferable that the vein side tubular member 340 is accommodated in the lumen 101 on the distal side of the puncture member 100 and the lymphatic vessel side tubular member 330 is accommodated in the vein side tubular member 340 on the proximal side (i.e., the vein side tubular member 340 is distal to the lymphatic vessel side tubular member 330 when the tubular members 330, 340 are in the lumen 101 of the puncture member 100).

Deformation Example 2

FIGS. 12A and 12B illustrate side-to-side anastomosis in which the tube wall L12 of the lymphatic vessel L and the tube wall P12 of the vein P are joined together by using the lymphatic vessel side tubular member 130 and the vein side tubular member 340.

In the side-to-side anastomosis according to the present deformation example, as illustrated in FIGS. 12A and 12B, the tube wall L12 of the lymphatic vessel L and the tube wall P12 of the vein P are joined together by interlocking the lymphatic vessel side tubular member 130 (which is fixed to the puncture site t formed in the tube wall L12 of the lymphatic vessel L) and the vein side tubular member 340 (which is fixed to the puncture site t formed in the tube wall P12 of the vein P) with each other.

The side-to-side anastomosis according to the present deformation example can be performed by using the medical apparatus 10. Specifically, the procedure is performed through the following process.

First, the puncture site t is formed in the tube wall L12 of the lymphatic vessel L by using the puncture member 100, and the lymphatic vessel side tubular member 130 is fixed to the puncture site t.

Subsequently, the puncture site t is formed in the tube wall P12 of the vein P by using the puncture member 100, and the vein side tubular member 340 is fixed to the puncture site t.

Subsequently, a portion exposed from the tube wall L12 of the lymphatic vessel L in the lymphatic vessel side tubular member 130 is inserted into the lumen of the vein side tubular member 340. The lymphatic vessel side tubular member 130 and the vein side tubular member 340 are thus mechanically interlocked with one another, and so the lymphatic vessel L and the vein P are joined together. In this case, the interlocking position of the lymphatic vessel side tubular member 130 and the vein side tubular member 340 is disposed outside the lymphatic vessel L and the vein P (i.e., the interlocking location is external of both the lymphatic vessel L and the vein P).

When the side-to-side anastomosis according to the present deformation example is performed, similar to a case of performing the side-to-end anastomosis, a flow path of lymph is created from the lymphatic vessel L side to the vein P side. Accordingly, it is possible to resolve accumulation of lymph causing lymphedema. In addition, a flow path of lymph is formed from the upstream La side of the lymphatic vessel L to the vein P and a flow path of lymph is formed from the downstream Lb side of the lymphatic vessel L to the vein P. Accordingly, it is possible to efficiently resolve accumulation of lymph.

In the side-to-side anastomosis according to the present deformation example, the order of procedures can be changed to fix the lymphatic vessel side tubular member 130 to the lymphatic vessel L after the vein side tubular member 340 is fixed to the vein P. In addition, the positional relationship between the lymphatic vessel side tubular member 130 and the vein side tubular member 340 to be disposed in the lumen 101 of the puncture member 100 can be appropriately changed in accordance with the order of performing fixing (i.e., the lymphatic vessel side tubular member 130 can be positioned either proximally or distally of the vein side tubular member 340 depending on which tubular member 130, 340 is to be released first).

Deformation Example 3

FIGS. 13A and 13B illustrate end-to-end anastomosis in which the opening end L31 of the lymphatic vessel L and the opening end P31 of the vein P are joined together by using the lymphatic vessel side tubular member 330 and the vein side tubular member 340.

In the end-to-end anastomosis according to the present deformation example, as illustrated in FIGS. 13A and 13B, the opening end L31 of the lymphatic vessel L and the opening end P31 of the vein P are joined together by interlocking the lymphatic vessel side tubular member 330 (which is fixed to the vicinity of the opening end L31 of the lymphatic vessel L) and the vein side tubular member 140 (which is fixed to the vicinity of the opening end P31 of the vein P) with each other.

The end-to-end anastomosis according to the present deformation example can be performed by using the medical apparatus 10. Specifically, the procedure is performed through the following process.

First, the lymphatic vessel side tubular member 330 is inserted and fixed with respect to the opening end L31 of the lymphatic vessel L by using the puncture member 100.

Subsequently, the vein side tubular member 140 is inserted and fixed with respect to the opening end P31 of the vein P by using the puncture member 100.

Subsequently, a portion exposed from the opening end L31 of the lymphatic vessel L in the lymphatic vessel side tubular member 330 is inserted into the lumen of the vein side tubular member 140. The lymphatic vessel side tubular member 330 and the vein side tubular member 140 are thus mechanically interlocked with one another, and so the lymphatic vessel L and the vein P are joined together.

When the end-to-end anastomosis according to the present deformation example is performed, similar to a case of performing the side-to-end anastomosis, a flow path of lymph is formed from the lymphatic vessel L side to the vein P side. Accordingly, it is possible to resolve accumulation of lymph causing lymphedema. In addition, the lymphatic vessel L and the vein P are joined together without forming the puncture site t in either the lymphatic vessel L or the vein P. Accordingly, it is possible to realize the less-invasive technique.

In the end-to-end anastomosis according to the present deformation example, the order of procedures can be changed to fix the lymphatic vessel side tubular member 330 to the lymphatic vessel L after the vein side tubular member 140 is fixed to the vein P. In addition, the positional relationship between the lymphatic vessel side tubular member 330 and the vein side tubular member 140 in the lumen 101 of the puncture member 100 can be appropriately changed in accordance with the order of performing fixing (i.e., the lymphatic vessel side tubular member 330 can be positioned either proximally or distally of the vein side tubular member 340 depending on which tubular member 330, 340 is to be released first). Moreover, when using the medical apparatus 10 to install the tubular member at only the end portion of the body lumens (i.e., in the end-to-end anastomosis according to the present deformation example), there is no need to perform puncturing using the puncture member 100. Therefore, it is possible to omit the installation of the puncture member 100 or the negative pressure generation member 180. In this case, when the medical apparatus is configured to include the plunger 150 and the lumen 101 in which the tubular member is accommodated, indwelling of the tubular member can be performed, and the structure of the medical apparatus can be appropriately modified as necessary.

As described above, the method of treating lymphedema according to Deformation Example 1 includes an end-to-side joining step (end-to-side anastomosis step) of joining the opening end of the lymphatic vessel and the tube wall of the vein together via the tubular member fixed to the opening end of the lymphatic vessel and the tubular member fixed to the tube wall of the vein.

The method of treating lymphedema according to Deformation Example 2 includes a side-to-side joining step (side-to-side anastomosis step) of joining the tube wall of the lymphatic vessel and the tube wall of the vein together via the tubular member fixed to the tube wall of the lymphatic vessel and the tubular member fixed to the tube wall of the vein.

The method of treating lymphedema according to Deformation Example 3 includes an end-to-end joining step (end-to-end anastomosis step) of joining the opening end of the lymphatic vessel and the opening end of the vein together via the tubular member fixed to the opening end of the lymphatic vessel and the tubular member fixed to the opening end of the vein.

When performing the side-to-end anastomosis, the end-to-side anastomosis, the side-to-side anastomosis, and the end-to-end anastomosis, the medical apparatus 10 does not have to be used, except for when the step of fixing the tubular member is performed successively after the step of puncturing the tube wall of the body lumen. As an example, the step of fixing the tubular member to the opening end of the body lumen can be performed by using known forceps or the like without using the medical apparatus 10.

The procedure described above starts from a preparation state where the two tubular members 130, 140 are accommodated in the lumen 101 of the puncture member 100 in advance. Each of the tubular members 130, 140 is then fixed successively (i.e., one after the other) after the step of puncturing the tube wall of the body lumen when performing the side-to-end anastomosis, the end-to-side anastomosis, the side-to-side anastomosis, and the end-to-end anastomosis. However, for example, it is possible to accommodate each of the tubular members 130, 140 in a different medical tool (for example, a tubular medical tool other than the puncture member 100) and to perform fixing each of the tubular members 130, 140 by using the different medical tool. As an example, each of the tubular members 130 and 140 may indwell (i.e., be fixed) by using the lymphatic vessel side tubular member 130 accommodated in the puncture member 100 and the vein side tubular member 140 accommodated in another medical tool different from the puncture member 100. In this case, the indwelling order of the lymphatic vessel side tubular member 130 and the vein side tubular member 140 can be appropriately changed.

In a case where the technique is performed by using a plurality of the tubular members, the interlocking position of each tubular member will be outside the body lumens (the lymphatic vessel L and the vein P) when performing the side-to-side anastomosis (e.g., as illustrated in FIGS. 12A and 12B). Therefore, in consideration of indwelling characteristics of the tubular member, it is preferable that the plurality of the tubular members are applied to the end-to-side anastomosis illustrated in FIGS. 11A and 11B or the end-to-end anastomosis illustrated in FIGS. 13A and 13B. Moreover, since indwelling of the tubular member can be more simply performed in a case where the tubular members are applied to the end-to-side anastomosis illustrated in FIGS. 11A and 11B or to the above-described side-to-end anastomosis (refer to FIGS. 10A and 10B) compared to a case where the tubular members are applied to the end-to-end anastomosis illustrated in FIGS. 13A and 13B, it is more preferable that the tubular members are applied to the end-to-side anastomosis or the side-to-end anastomosis (i.e., the indwelling of the tubular members is more easily performed in end-to-side or side-to end anastomosis than in end-to-end anastomosis.

Modification examples of the tubular member are described next. In the below descriptions of each modification example, a procedure of using the medical apparatus 10, a configuration of the medical apparatus 10, and the like, any description already explained above in regards to the above-described embodiment will be omitted. In the description of each modification example, description of a similar procedure, a similar configuration, and the like will be appropriately omitted.

A lymphatic vessel side tubular member 130a according to Modification Examples 1 to 6 described below is different from the above-described lymphatic vessel side tubular member 130 in the configuration of the coming-off prevention portion (i.e., the portion that prevents the tubular member from coming off from the tube wall L12 of the lymphatic vessel L). In the description of each modification example, the side-to-end anastomosis procedure is used as an example of the technique in which the lymphatic vessel side tubular member 130a is used. Hereinafter, each modification will be described in detail.

Modification Example 1

FIGS. 14A and 14B illustrate the lymphatic vessel side tubular member 130a according to Modification Example 1 and conditions before and after the lymphatic vessel side tubular member 130a is fixed to the lymphatic vessel L.

A coming-off prevention portion 417 included in the lymphatic vessel side tubular member 130a of the present modification example is configured to be able to perform expanding deformation (i.e., expand) in a direction intersecting a protrusion direction (radially outward from the lymphatic vessel side tubular member 130a) in accordance with protruding from the distal opening portion 103 of the puncture member 100 (i.e., the coming-off prevention portion 417 itself expands radially outward relative to the lymphatic vessel side tubular member 130a).

As illustrated in FIG. 14A, the coming-off prevention portion 417 is pressed by the inner surface of the puncture member 100 (i.e., the inner surface of the puncture member 100 applies a force to the coming-off prevention portion 417 to contract the coming-off prevention portion 417 radially inward) when the coming-off prevention portion 417 is accommodated in the lumen 101 of the puncture member 100. The coming-off prevention portion 417 is in the contracted state in this configuration.

As illustrated in FIG. 14B, when the coming-off prevention portion 417 protrudes from the distal opening portion 103 of the puncture member 100, the coming-off prevention portion 417 performs expanding deformation in the direction intersecting the protrusion direction (i.e., the coming-off prevention portion 417 expands radially outward). The coming-off prevention portion 417 thus applies an engagement force against the inner surface L12b of the tube wall L12 of the lymphatic vessel L. Accordingly, it is possible to stably maintain a state where the lymphatic vessel side tubular member 130a is fixed to the lymphatic vessel L.

For example, the coming-off prevention portion 417 can be configured to be made from an elastic member which performs expanding deformation (i.e., radially outward expansion) in accordance with protruding from the distal opening portion 103 of the puncture member 100. Examples of materials that can be used for the coming-off prevention portion 417 include various types of rubber materials such as natural rubber, butyl rubber, isoprene rubber, butadiene rubber, styrene-butadiene rubber, styrene-ethylene-butylene styrene rubber, and silicone rubber; various types of thermoplastic elastomers such as a polyurethane-based elastomer, a polyester-based elastomer, a polyamide-based elastomer, an olefin-based elastomer, and a styrene-based elastomer; mixtures thereof; and the like.

The coming-off prevention portion 417 is formed to have a ring shape while being disposed throughout the entirety of the outer circumferential surface of the lymphatic vessel side tubular member 130a. However, the shape is not limited to such a shape. For example, it is possible to intermittently dispose the coming-off prevention portions 417 at intervals in the circumferential direction of the outer surface of the lymphatic vessel side tubular member 130a. The cross-sectional shape can also be appropriately changed as long as the function of preventing the lymphatic vessel side tubular member 130a from coming off from the lymphatic vessel L is not impaired. Thus, the cross-sectional shape is not limited to the illustrated shape.

The coming-off prevention portion 417 according to the present modification example is configured to perform expanding deformation (i.e., expand radially outward) when protruding from the distal opening portion 103 of the puncture member 100. Therefore, the coming-off prevention portion 417 can be accommodated in a compact manner in a state of being accommodated in the lumen 101 of the puncture member 100 and can apply the engagement force to sufficiently act on the lymphatic vessel L in order to prevent coming-off (i.e., to prevent the lymphatic vessel side tubular member 130 from being removed from the lymphatic vessel L) when the coming-off prevention portion 417 is inside the lymphatic vessel L. Accordingly, in the lymphatic vessel side tubular member 130a according to the present modification example, it is possible to further improve accommodation characteristics with respect to the lumen 101 of the puncture member 100 and the function of preventing coming-off with respect to the lymphatic vessel L.

Modification Example 2

FIG. 15A illustrates the lymphatic vessel side tubular member 130a according to Modification Example 2 and a condition when the lymphatic vessel side tubular member 130a is fixed to the lymphatic vessel L.

The lymphatic vessel side tubular member 130a according to the present modification example includes a first coming-off prevention portion 427a and a second coming-off prevention portion 427b which are respectively disposed at positions different from each other in the lymphatic vessel side tubular member 130a in the extending direction (i.e., the vertical direction in the FIG. 15A, which is also the extending direction of the puncture member 100 and the lymphatic vessel side tubular member 130a). Similar to the above-described coming-off prevention portion 417 according to Modification Example 1, each of the coming-off prevention portions 427a, 427b is configured to be able to perform expanding deformation in the direction intersecting the protrusion direction in accordance with protruding from the distal opening portion 103 of the puncture member 100.

The first coming-off prevention portion 427a is disposed on the distal side of the lymphatic vessel side tubular member 130a closer than the second coming-off prevention portion 427b (on the distal side of the lymphatic vessel L in the insertion direction). Similar to the above-described coming-off prevention portion 417 according to Modification Example 1, for example, each of the coming-off prevention portions 427a, 427b can be configured to be made from an elastic member which can perform expanding deformation.

Each of the coming-off prevention portions 427a, 427b is pressed by the inner surface of the puncture member 100 when the lymphatic vessel side tubular member 130a is in the lumen 101 of the puncture member 100. In this position, the coming-off prevention portions 427a, 427b are in the contracted state.

As illustrated in FIG. 15A, when each of the coming-off prevention portions 427a, 427b protrudes from the distal opening portion 103 of the puncture member 100, each of the coming-off prevention portions 427a, 427b performs expanding deformation in the direction intersecting the protrusion direction (i.e., the coming-off prevention portions 427a, 427b expand radially outward). The first coming-off prevention portion 427a which has expanded radially outward applies an engagement force on the inner surface L12b of the tube wall L12 of the lymphatic vessel L to prevent coming-off (i.e., to indwell the lymphatic vessel side tubular member 130a in the lymphatic vessel L). Meanwhile, the second coming-off prevention portion 427b which has expanded radially outward applies an engagement force on the outer surface L12a of the tube wall L12 of the lymphatic vessel L in order to prevent coming-off (i.e., to indwell the lymphatic vessel side tubular member 130a in the lymphatic vessel L). Since each of the coming-off prevention portions 427a, 427b is disposed to pinch the tube wall L12 of the lymphatic vessel L from the outer surface L12a side and the inner surface L12b side (i.e., apply an engagement force on the outer surface L12a and on the inner surface L12a), it is possible to more stably fix the lymphatic vessel side tubular member 130a to the lymphatic vessel L.

A distance between the first coming-off prevention portion 427a and the second coming-off prevention portion 427b can be appropriately set within a range to correspond to the thickness of the tube wall L12 of the lymphatic vessel L.

Modification Example 3

FIG. 15B illustrates the lymphatic vessel side tubular member 130a according to Modification Example 3 and a condition when the lymphatic vessel side tubular member 130a is fixed to the lymphatic vessel L.

The lymphatic vessel side tubular member 130a according to the present modification example includes a coming-off prevention portion 437 which is configured to have a cross-sectional shape tapered toward the inner surface L12b of the lymphatic vessel L (reversal shape). The coming-off prevention portion 437 causes engagement force to act on the inner surface L12b of the tube wall L12 of the lymphatic vessel L in order to prevent coming-off (i.e., indwelling the lymphatic vessel side tubular member 130a in the lymphatic vessel L) by causing the distal end to bite into the inner surface L12b. Accordingly, hooking properties with respect to the inner surface L12b of the tube wall L12 of the lymphatic vessel L can be strengthened, and thus, it is possible to more favorably prevent the lymphatic vessel side tubular member 130a from coming off from the lymphatic vessel L.

As illustrated in the present modification example, the cross-sectional shape of the coming-off prevention portion 437 can be appropriately changed in consideration of the engagement force caused to act on the lymphatic vessel L, insertion characteristics with respect to the inside of the lymphatic vessel L, or the like.

Similar to the above-described coming-off prevention portion 417 according to Modification Example 1, the coming-off prevention portion 437 is configured to be able to perform expanding deformation (i.e., expand radially outward) in the direction intersecting the protrusion direction when protruding from the distal opening portion 103 of the puncture member 100.

Modification Example 4

FIGS. 16A and 16B illustrate the lymphatic vessel side tubular member 130a according to Modification Example 4. FIGS. 16A and 16B show the conditions before and after the lymphatic vessel side tubular member 130a is fixed to the lymphatic vessel L.

A coming-off prevention portion 447 included in the lymphatic vessel side tubular member 130a of the present modification example is configured to be made from a vane (belt-like) member which performs expanding deformation (i.e., expands radially outward) in the direction intersecting the protrusion direction when the coming-off prevention portion 447 protrudes from the distal opening portion 103 of the puncture member 100.

For example, the coming-off prevention portion 447 can be a thin plate member made from a super-elastic alloy or the like. As the super-elastic alloy, for example, it is possible to use one of the materials listed as possibilities for the lymphatic vessel side tubular member 130 material in the above-described embodiment.

As illustrated in FIG. 16A, when the coming-off prevention portion 447 is in a state of being accommodated in the lumen 101 of the puncture member 100, the coming-off prevention portion 447 is pressed by the inner surface of the puncture member 100 (i.e., the inner surface of the puncture member 100 applies a force to the coming-off prevention portion 447 to hold it in a contracted/folded state). In this position, the coming-off prevention portion 447 is in a folded state.

As illustrated in FIG. 16B, when the coming-off prevention portion 447 protrudes from the distal opening portion 103 of the puncture member 100, the coming-off prevention portion 447 is deployed in the direction intersecting the protrusion direction, thereby performing expanding deformation (i.e., expansion radially outward). The coming-off prevention portion 417 which expands radially outward applies an engagement force on the inner surface L12b of the tube wall L12 of the lymphatic vessel L in order to prevent coming-off (i.e., indwelling the lymphatic vessel side tubular member 130a in the lymphatic vessel L).

Since the coming-off prevention portion 447 according to the present modification example is configured to be made from the vane member, the coming-off prevention portion 447 can be accommodated inside the lumen 101 of the puncture member 100 in a compact manner in the folded state. Moreover, when expanding deformation is performed, the coming-off prevention portion 447 is deployed so as to extend radially outward. Therefore, it is possible to increase the amount of attachment with respect to the inner surface L12b of the tube wall L12 of the lymphatic vessel L. Accordingly, in the lymphatic vessel side tubular member 130a according to the present modification example, it is possible to further improve accommodation characteristics with respect to the lumen 101 of the puncture member 100 and the function of preventing coming-off with respect to the lymphatic vessel L.

Modification Example 5

FIGS. 17A and 17B illustrate the lymphatic vessel side tubular member 130a according to Modification Example 5. FIGS. 17A and 17B show the conditions before and after the lymphatic vessel side tubular member 130a is fixed to the lymphatic vessel L.

A coming-off prevention portion 457 included in the lymphatic vessel side tubular member 130a of the present modification example is configured to be made from a swelling member which swells in the direction intersecting the protrusion direction (i.e., a radially outward direction) when the coming-off prevention portion 457 protrudes from the distal opening portion 103 of the puncture member 100.

For example, the swelling member can be made from a gel which swells when contacting a body fluid such as lymph, or a gel which swells in response to external stimuli such as a body temperature, pH, and the like. Examples of materials to use as the swelling member include gels made from a water-absorbing polymer, a high water-absorbing resin, and the like; PNIPAM which swells in reaction to a body temperature or pH; and the like.

As illustrated in FIG. 17A, the coming-off prevention portion 457 maintains the contracted state when in a state of being accommodated in the lumen 101 of the puncture member 100, that is, a state before being in contact with a body fluid such as lymph.

As illustrated in FIG. 17B, When the coming-off prevention portion 457 protrudes from the distal opening portion 103 of the puncture member 100 and comes into contact with a body fluid (such as lymph), the coming-off prevention portion 457 swells in the direction intersecting the protrusion direction (i.e., expands radially outward). The coming-off prevention portion 457 which has swelled (i.e., expanded radially outward) applies an engagement force on the inner surface L12b of the tube wall L12 of the lymphatic vessel L in order to prevent coming-off (i.e. to prevent the lymphatic side tubular vessel 130a from being removed from the lymphatic vessel L). Accordingly, it is possible to stably fix the lymphatic vessel side tubular member 130a to the lymphatic vessel L.

The coming-off prevention portion 457 according to the present modification example swells when contacting a body fluid such as lymph. Therefore, the coming-off prevention portion 457 also functions as a cushioning member which weakens the pressing force applied to the tube wall L12 of the lymphatic vessel L in such a case where force in a direction in which the lymphatic vessel side tubular member 130a comes off from the lymphatic vessel L acts. Therefore, it is possible to reduce the load applied to the lymphatic vessel L while the lymphatic vessel side tubular member 130a is fixed to the lymphatic vessel L.

For example, the coming-off prevention portion 457 can be configured to be able to perform expanding deformation (i.e., expand radially outward) independently from the lymphatic vessel side tubular member 130a by using a member other than the swelling member. For example, the coming-off prevention portion 457 can be a shape memory alloy, a shape memory polymer, or the like.

Modification Example 6

FIGS. 18A and 18B illustrate the lymphatic vessel side tubular member 130a according to Modification Example 6. FIGS. 18A and 18B show the conditions before and after the lymphatic vessel side tubular member 130a is fixed to the lymphatic vessel L.

A coming-off prevention portion 467 included in the lymphatic vessel side tubular member 130a of the present modification example is configured to be able to perform expanding deformation in the direction intersecting the protrusion direction (i.e., expand radially outward) when the coming-off prevention portion 467 protrudes from the distal opening portion 103 of the puncture member 100. In addition, an uneven groove portion 468 is on the outer surface of the coming-off prevention portion 467 to enhance the engagement force applied to the tube wall L12 of the lymphatic vessel L.

For example, the coming-off prevention portion 467 can be configured to be made from an elastic material or the like. For example, the groove portion 468 can be configured to be a spiral screw groove which is formed in ordinary female screws, male screws, and the like.

The coming-off prevention portion 467 is pressed by the inner surface of the puncture member 100 when the lymphatic vessel side tubular member 130a is accommodated in the lumen 101 of the puncture member 100, thereby being in the contracted state.

As illustrated in FIG. 18A, when fixing the lymphatic vessel side tubular member 130a to the lymphatic vessel L, the puncture member 100 is rotated while the coming-off prevention portion 467 is exposed from the distal opening portion 103 of the puncture member 100. The coming-off prevention portion 467 performs expanding deformation in accordance with protruding from the distal opening portion 103 and causes the groove portion 468 which is formed on the outer surface to bite into the inner surface L12b of the tube wall L12 of the lymphatic vessel L. As a result of these puncture member 100 rotation operations, the engagement force applied by the coming-off prevention portion 467 on the inner surface L12b of the tube wall L12 of the lymphatic vessel L is enhanced. Therefore, it is possible to more stably fix the lymphatic vessel side tubular member 130a to the lymphatic vessel L.

As illustrated in FIG. 18B, after the lymphatic vessel side tubular member 130a is fixed to the lymphatic vessel L, the puncture member 100 is appropriately caused to retreat from the lymphatic vessel L.

It is preferable that a shape of the axially orthogonal cross section in the puncture member 100 is formed to have an incomplete round shape such as an elliptical shape, for example, so as to be able to cause the groove portion 468 to efficiently bite into the inner surface L12b of the tube wall L12 of the lymphatic vessel L by operating the coming-off prevention portion 467 to rotate. Similarly, it is preferable that the shape of the axially orthogonal cross section in the lymphatic vessel side tubular member 130a is also formed to have an incomplete round shape such as an elliptical shape.

In the description of each modification example, description is given regarding an example of performing the side-to-end anastomosis in which the lymphatic vessel side tubular member 130a is used. However, the lymphatic vessel side tubular member 130a according to each modification example can also be used in the side-to-side anastomosis and the end-to-side anastomosis. In addition, each of the coming-off prevention portions described in the modification examples above can also be provided in the vein side tubular member which is used when performing the side-to-side anastomosis or the end-to-side anastomosis. Moreover, an arbitrary combination of each of the coming-off prevention portions described in the modification examples above can also be included in the lymphatic vessel side tubular member or the vein side tubular member.

Subsequently, a tubular member according to an alternative embodiment will be described. In the below description of the present embodiment, a procedure of using the medical apparatus 10, a configuration of the medical apparatus 10, and the like, descriptions similar to those in the above-described first embodiment and each of the modification examples are omitted.

FIGS. 19A and 19B illustrate a tubular member 530 according to the present embodiment and conditions when the side-to-end anastomosis is performed by using the tubular member 530.

The tubular member 530 according to the present embodiment is configured to be able to join the lymphatic vessel L and the vein P together by using one tubular member 530.

The tubular member 530 includes a lumen 531, a distal opening portion 533 at the distal end of the lumen 531, a proximal opening portion 535 at the proximal end of the lumen 531, and a coming-off prevention portion 537 at the distal end of the tubular member 530.

The basic structure related to the configuration material and the like of the tubular member 530 is similar to that of the lymphatic vessel side tubular member 130 according to the above-described first embodiment. However, a length Lm of the tubular member 530 in the axial direction is longer than the lymphatic vessel side tubular member 130. The longer length allows the tubular member 530 to join the lymphatic vessel L and the vein P together without applying the vein side tubular member 140 and interlocking two tubular members 130, 140.

As illustrated in FIG. 19A, when the tubular member 530 is accommodated in the lumen 101 of the puncture member 100, the tubular member 530 contracts inwardly in the radial direction. The tubular member 530 performs expanding deformation (i.e., expands radially outward) when released from the distal opening portion 103 of the puncture member 100.

As illustrated in FIG. 19B, the tubular member 530 is fixed in a state where a side wall 538 is attached to the inner surface of the puncture site t while being in a state of being inserted into the puncture site t (i.e., the inner wall of the lymphatic vessel L) which has been created by the needle tip 107 of the puncture member 100. When the lymphatic vessel L and the vein P are joined together, the proximal portion of the tubular member 530 is inserted into the opening end P31 of the vein P while being in a state where the distal portion of the tubular member 530 is fixed to the lymphatic vessel L. The lymphatic vessel L and the vein P are joined together via the tubular member 530.

The proximal portion of the tubular member 530 is formed to have a tapered shape of which the outer diameter decreases in diameter toward the proximal side. The proximal portion of the tubular member 530 can be easily inserted into the opening end P31 of the vein P by forming the proximal portion of the tubular member 530 to have a tapered shape.

As described in the present embodiment, even when performing the side-to-end anastomosis by using one tubular member 530, a flow of lymph leading from the lymphatic vessel L side to the vein P side can be formed. Accordingly, it is possible to resolve accumulation of lymph causing lymphedema. In addition, since the side-to-end anastomosis is performed by using the medical apparatus 10, there is no need to form the minute window portion in the lymphatic vessel L by performing procedures of incision or the like. Accordingly, it is possible to promptly and easily perform the procedure. The number of steps for fixing the tubular member to the body lumen can thus be reduced compared to the procedure in which the lymphatic vessel L and the vein P are joined together by using the plurality of tubular members. Accordingly, it is possible to further shorten the time required for the procedure.

In the description of the present embodiment, description is given regarding an example of performing the side-to-end anastomosis in which one tubular member 530 is used. However, the tubular member 530 according to the present embodiment can also be used in the side-to-side anastomosis, the end-to-side anastomosis, and the end-to-end anastomosis. In addition, each of the coming-off prevention portions respectively described in the above-referenced modification examples can also be included in the tubular member 530 according to the present embodiment. When being performed using one tubular member 530, it is preferable that the tubular member 530 is applied to the end-to-side anastomosis or the side-to-end anastomosis from the viewpoint of indwelling characteristics.

The medical apparatus and the method of treating lymphedema according to the invention are described above in regards to a plurality of the embodiments and a plurality of the modification examples. However, the invention is not limited to only the configuration, the procedure (technique), or the steps described in each of the embodiments and each of the deformation examples. The invention can be appropriately changed based on the disclosed aspects of the invention.

For example, description is given regarding an example in which the negative pressure generation member is configured by the valve body which causes suctioning pressure to act in accordance with sliding. However, the configuration of the negative pressure generation member is not particularly limited as long as negative pressure can be generated in the space portion which is defined by the outer tube. For example, a valve body which can switch the communication status of the inside and the outside of outer tube can be added to the outer tube (i.e., opening this valve body can allow the outer tube to communicate with the environment outside the outer tube). It is also possible to use suctioning means configured to interlock with the valve body in an airtight manner as the negative pressure generation member. A known mechanism for interlocking a negative pressure tube such as a syringe pump, a vacuum pump, and a vacuum blood collection tube can be used, for example, as the suctioning means.

In the medical apparatus according to the invention, the configuration of each portion can be appropriately changed and additional members can be appropriately added and omitted as long as the medical apparatus is configured to be able to form a puncture site by puncturing the tube wall of the body lumen which becomes the joining target, and the tubular member which can perform expanding deformation (i.e., expand radially outward) and contracting deformation (i.e., contract radially inward) is disposed at the puncture site so that the body lumens can be joined together by using the tubular member.

The detailed description above describes a medical apparatus and method for treating lymphedema. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical apparatus for joining a first body lumen in a living body to a second body lumen in the living body so that the first and second body lumens communicate with one another, the medical apparatus comprising:
    a puncture member comprising an inner wall that defines a lumen and a distal opening portion at a distal end of the lumen forming a needle tip at the distal end of the lumen, the needle tip configured to puncture a wall surrounding the first body lumen to form a puncture site, the distal opening portion formed as the needle tip possessing an uninterrupted outer circumference;
    a tubular member positioned in the lumen of the puncture member while the tubular member is in a contracted state in which the tubular member is contracted radially inward and being movable to a position outside the lumen of the puncture member to cause the tubular member to expand radially outward from the contracted state to an expanded state;
    the tubular member being comprised of a side wall surrounding a lumen that passes throughout the tubular member from a distal edge of the side wall to a proximal edge of the side wall, the tubular member including a slit that extends from the distal edge of the side wall to the proximal edge of the side wall so that the tubular member includes first and second separated end portions that each extend from the distal edge of the side wall to the proximal edge of the side wall, the first and second end portions each possessing an inner peripheral surface and an outer peripheral surface, the inner peripheral surface of the first end portion overlapping the outer peripheral surface of the second end portion when the tubular member is positioned in the lumen of the puncture member and is in the contracted state;
    a plunger that is movably positioned in the lumen of the puncture member, the plunger being movable relative to the puncture member to release the tubular member from the distal opening portion of the puncture member so that the tubular member is moved to a position outside the lumen of the puncture member and passing through the puncture site in the tube wall surrounding the first body lumen so that the first body lumen communicates outside the first lumen by way of the lumen in the tubular member;
    the tubular member contacting the inner wall of the puncture member while the tubular member is accommodated in the lumen of the puncture member to hold the tubular member in the contracted state, the tubular member expanding toward the expanded state to be fixed at the puncture site in the tube wall surrounding the first body lumen when the tubular member is released from the distal opening portion of the puncture member by the plunger moving relative to the puncture member; and
    an outer tube surrounding an outer circumferential surface of the puncture member and defining a space portion between the puncture member and the tube wall of the body lumen when the needle tip punctures the tube wall of the body lumen.

2. The medical apparatus according to claim 1, further comprising:
    a negative pressure generation member configured to displace the tube wall of the first body lumen toward the needle tip of the puncture member and through the distal opening portion by generating negative pressure in the space portion, the puncture member including a central axis that passes through the distal opening portion.

3. The medical apparatus according to claim 2, wherein the negative pressure generation member has a valve body which is slidably movable within the lumen of the puncture member, the valve body generating the negative pressure in the space portion when the valve body slides in a proximal direction of the puncture member.

4. The medical apparatus according to claim 1, wherein the tubular member comprises a coming-off prevention portion configured to apply an engagement force on the tube wall of the first body lumen, the engagement force applied by the coming-off prevention portion of the tubular member to fix the tubular member at the puncture site in the tube wall surrounding the first body lumen.

5. The medical apparatus according to claim 4, wherein the coming-off prevention portion is configured to expand radially outward relative to the tubular member when the coming-off prevention portion protrudes from the distal opening portion of the puncture member.

6. The medical apparatus according to claim 5, wherein
    the tubular member includes a second coming-off prevention portion which is disposed at a different position than the coming-off prevention portion in an extending direction of the tubular member; and
    the coming-off prevention portion engages an inner surface of the tube wall of the first body lumen and the second coming-off prevention portion engages an outer surface of the tube wall of the first body lumen.

7. The medical apparatus according to claim 1, further comprising:

an interlocking tubular member in the lumen of the puncture member positioned proximal to the tubular member, and being configured to expand radially outward and to contract radially inward, and being configured to interlock with the tubular member.

8. The medical apparatus according to claim 7, wherein the interlocking tubular member comprises a lumen and possesses an inner diameter; the tubular member possesses an outer diameter; and when the tubular member and the interlocking tubular member have expanded radially outward, the inner diameter of the interlocking tubular member is greater than the outer diameter of the tubular member.

9. The medical apparatus according to claim 1, wherein an entirety of the puncture member is a rigid plastic cylindrical body, the needle tip being a beveled tip of the rigid plastic cylindrical body.

10. A medical apparatus for joining a first lumen in a living body to a second lumen in the living body so that the first and second lumens communicate with one another, the medical apparatus comprising: a puncture member extending in an axial direction and possessing a proximal end, a distal end and an outer circumferential surface, the puncture member comprising a lumen surrounded by an inner wall of the puncture member, a needle tip at the distal end of the puncture member, and a distal opening portion formed as the needle tip at the distal end of the puncture member, an entirety of the puncture member being a rigid plastic cylindrical body, the needle tip being a beveled tip of the rigid plastic cylindrical body, the puncture member possessing a central axis that passes through the distal opening portion, the puncture member being movable in the axial direction to cause the beveled tip to puncture a wall surrounding the first lumen in the living body to form a puncture site, the inner wall of the puncture member being a part of the puncture member so that the inner wall of the puncture member moves with the puncture member whenever the puncture member moves; an outer tube surrounding the outer circumferential surface of the puncture member, the outer tube comprising a distal opening portion configured to contact the wall of the first lumen, the distal opening portion of the outer tube being in contact with the wall of the first lumen to define a space between the puncture member and the wall of the first lumen when the needle tip punctures the wall of the first lumen; a first tubular member positioned in the lumen of the puncture member, the first tubular member configured to expand radially outward and to contract radially inward, the first tubular member positioned in the lumen of the puncture member being in a contracted state in which the first tubular member is contracted radially inward by virtue of the first tubular member contacting the inner wall of the puncture member, the first tubular member positioned in the lumen of the puncture member being movable to a position outside the lumen of the puncture member in which the first tubular member expands radially outward from the contracted state to an expanded state and passes through the puncture site in the wall surrounding the first lumen so that the first lumen communicates outside the first lumen by way of a lumen in the tubular member; a plunger movably positioned in the lumen of the puncture member, the plunger being movable in the axial direction relative to the puncture member to push the first tubular member in a distal direction so that the first tubular member is released from the distal opening portion of the puncture member and is at the position passing through the puncture site in the wall surrounding the first lumen; the first tubular member being expandable radially outwardly when the first tubular member is released from the distal opening portion to be at the position passing though the puncture site in the wall surrounding the first lumen; a negative pressure generation member configured to generate negative pressure in the space to pull the wall surrounding the first lumen toward the needle tip of the puncture member; a second tubular member positioned within the lumen of the puncture member at a position proximal of the first tubular member, the second tubular member being configured to expand radially outward and to contract radially inward, the second tubular member positioned in the lumen of the puncture member being in a contracted state in which the second tubular member is contracted radially inward by virtue of the second tubular member contacting the inner wall of the puncture member, the second tubular member positioned in the lumen of the puncture member being movable to a position outside the lumen of the puncture member in which the second tubular member expands radially outward from the contracted state to an expanded state; and the first tubular member possessing a distal-most end and a proximal-most end, the distal-most end of the first tubular member being closer to the needle tip than the proximal-most end of the first tubular member, the second tubular member possessing a distal-most end and a proximal-most end, the distal-most end of the second tubular member directly contacting the proximal-most end of the first tubular member, the second tubular member being moved in the axial direction by the movement of the plunger in the axial direction, and the movement of the second tubular member causing movement of the first tubular member in the axial direction as a result of the distal-most end of the second tubular member directly contacting the proximal-most end of the first tubular member.

11. The medical apparatus according to claim 10, wherein the first tubular member has a distal end and an outer wall surface; and
the distal end of the first tubular member comprises a protrusion, the protrusion having a greater outer diameter than the outer wall surface of the first tubular member when the first tubular member expands radially outward.

12. The medical apparatus according to claim 11, wherein the protrusion of the first tubular member applies a contact force on an inner wall surface of the wall surrounding the first lumen when the first tubular member is at the position passing through the puncture site, the contact force fixing the first tubular member in place at the puncture site in the wall surrounding the first lumen.

13. The medical apparatus according to claim 10, wherein the negative pressure generation member comprises a valve body that is slidably movable within the lumen of the puncture member, the valve body generating the negative pressure in the space when the valve body slides in a proximal direction of the puncture member.

14. The medical apparatus according to claim 13, wherein the valve body of the negative pressure generation member, the plunger, the lumen of the puncture member, and the outer tube are coaxial.

15. The medical apparatus according to claim 10, wherein the first tubular member has a hollow cylindrical shape and possesses an outer circumferential wall, a top edge, and a bottom edge; and
the outer circumferential wall includes a slit extending from the top edge of the first tubular member to the bottom edge of the first tubular member.

16. The medical apparatus according to claim 10 wherein the first tubular member possesses an outer diameter and the second tubular member possesses an outer diameter; the outer diameter of the first tubular member being equal to the outer diameter of the second tubular member when the first tubular member and the second tubular member are within the lumen of the puncture device member: and the outer diameter of the first tubular member being less than the outer diameter of the second tubular member when the first tubular member and the second tubular member are released from the distal opening portion of the puncture member.

17. A medical apparatus for joining a first lumen in a living body to a second lumen in the living body so that the first and second lumens communicate with one another, the medical apparatus comprising: a puncture member extending in an axial direction and possessing a proximal end, a distal end and an outer circumferential surface, the puncture member comprising a lumen surrounded by an inner wall of the puncture member, a needle tip at the distal end of the puncture member, and a distal opening portion formed as the needle tip at the distal end of the puncture member, an entirety of the puncture member being a rigid plastic cylindrical body, the needle tip being a beveled tip of the rigid plastic cylindrical body; the puncture member being movable in the axial direction to cause the beveled tip to puncture a wall of the first lumen surrounding the living body to form a puncture site in the wall surrounding the first lumen, the inner wall of the puncture member being a part of the puncture member so that the inner wall of the puncture member moves with the puncture member whenever the puncture member moves; an outer tube surrounding the outer circumferential surface of the puncture member, the outer tube comprising a distal opening portion configured to contact an outer surface of the wall surrounding the first lumen, the distal opening portion of the outer tube being in contact with the wall surrounding the first lumen to define a space between the puncture member and the wall of the body lumen when the needle tip punctures the wall surrounding the first lumen; a first tubular member positioned in the lumen of the puncture member, the first tubular member being configured to expand radially outward and to contract radially inward, the first tubular member positioned in the lumen of the puncture member being in a contracted state in which the first tubular member is contracted radially inward by virtue of the first tubular member contacting the inner wall of the puncture member, the first tubular member positioned in the lumen of the puncture member being movable to a position outside the lumen of the puncture member in which the first tubular member expands radially outward from the contracted state to an expanded state and passes through the puncture site in the wall surrounding the first lumen so that the first lumen communicates outside the first lumen by way of a lumen in the tubular member; a second tubular member positioned within the lumen of the puncture member at a position proximal of the first tubular member, the second tubular member being configured to expand radially outward and to contract radially inward, the second tubular member positioned in the lumen of the puncture member being in a contracted state in which the second tubular member is contracted radially inward, the second tubular member positioned in the lumen of the puncture member being movable to a position outside the lumen of the puncture member in which the second tubular member expands radially outward from the contracted state to an expanded state; a plunger movably positioned in the lumen of the puncture member at a position proximal of the second tubular member, the plunger being movable in the axial direction relative to the puncture member to push the first tubular member in a distal direction so that the first tubular member is released from the distal opening portion of the puncture member; and the second tubular member being comprised of a side wall surrounding a lumen that passes throughout the second tubular member from a distal edge of the side wall to a proximal edge of the side wall, the second tubular member including a slit that extends from the distal edge of the side wall to the proximal edge of the side wall so that the second tubular member includes first and second separated end portions that each extend from the distal edge of the side wall to the proximal edge of the side wall, the first and second end portions each possessing an inner peripheral surface and an outer peripheral surface, the inner peripheral surface of the first end portion of the second tubular member overlapping the outer peripheral surface of the second end portion of the second tubular member when the second tubular member is in the contracted state the lumen of the puncture member and is contracted radially inward.

18. A medical apparatus for joining first and second lumens in a living body, the medical apparatus comprising: a puncture member extending in an axial direction and possessing a proximal end, a distal end and an outer circumferential surface, the puncture member comprising a lumen surrounded by an inner wall of the puncture member, a needle tip at the distal end of the puncture member, and a distal opening at the distal end of the puncture member, the puncture member being movable toward the first lumen in the living body to puncture a lumen wall surrounding the first lumen and form a puncture site in the lumen wall; a tubular member positioned in the lumen of the puncture member, the tubular member being configured to expand radially outward and to contract radially inward, the tubular member positioned in the lumen of the puncture member being in a contracted state in which the tubular member is contracted radially inward by virtue of the tubular member contacting the inner wall of the puncture member, the tubular member being movable to outside the lumen of the puncture member and expanding radially outward from the contracted state to an expanded state when moved to outside the lumen of the puncture member, the tubular member possesses a proximal end and a distal end; a plunger positioned in the lumen of the puncture member for movement relative to the puncture member in the axial direction, the plunger being movable relative to the puncture member after the puncture member punctures the lumen wall to move the tubular member from inside the lumen in the puncture member to a position in which the tubular member is located in the puncture site in the lumen wall such that the distal end of the tubular member is positioned on one side of the lumen wall and the proximal end of the tubular member is positioned on an opposite side of the lumen wall so that the first lumen communicates outside the first lumen by way of a lumen passing through the tubular member, the one side of the lumen wall facing the first lumen and the opposite side of the lumen wall facing away from the first lumen; an outer tube surrounding the outer circumferential surface of the puncture member and defining a space portion between the puncture member and the lumen wall when the needle tip punctures the lumen wall; and the tubular member possessing a distal end portion at which is located a projection that projects radially outwardly from the tubular member and that is positioned on the one side of the lumen wall when the tubular member is located in the puncture site in the lumen wall to prevent the tubular member from being removed from the puncture site.

* * * * *